(12) United States Patent
Wang et al.

(10) Patent No.: US 11,890,077 B2
(45) Date of Patent: *Feb. 6, 2024

(54) APPARATUS, DEVICES AND METHODS FOR IN VIVO IMAGING AND DIAGNOSIS

(71) Applicant: The General Hospital Corporation, Boston, MA (US)

(72) Inventors: Hao Wang, Brookline, MA (US); Joseph A. Gardecki, Acton, MA (US); Guillermo J. Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 271 days.

This patent is subject to a terminal disclaimer.

(21) Appl. No.: 17/161,366

(22) Filed: Jan. 28, 2021

(65) Prior Publication Data

US 2021/0161387 A1 Jun. 3, 2021

Related U.S. Application Data

(63) Continuation of application No. 15/327,801, filed as application No. PCT/US2015/042283 on Jul. 27, 2015, now Pat. No. 10,912,462.
(Continued)

(51) Int. Cl.
*A61B 5/00* (2006.01)
*A61B 5/055* (2006.01)
(Continued)

(52) U.S. Cl.
CPC .......... *A61B 5/0071* (2013.01); *A61B 5/0035* (2013.01); *A61B 5/0066* (2013.01);
(Continued)

(58) Field of Classification Search
CPC ... A61B 5/0071; A61B 5/0035; A61B 5/0066; A61B 5/0084; A61B 5/0086;
(Continued)

(56) References Cited

U.S. PATENT DOCUMENTS 5,935,075 A * 8/1999 Casscells ............. A61B 5/0086
600/549
7,672,713 B2 3/2010 Furnish
(Continued)

FOREIGN PATENT DOCUMENTS

JP 2001104237 A 4/2001
JP 2001161696 A 6/2001
(Continued)

OTHER PUBLICATIONS

Korean Intellectual Property Office. Notice of Grounds for Rejection for application 10-2017-7005420, dated Nov. 27, 2021. With translation. 20 pages.
(Continued)

*Primary Examiner* — Sanjay Cattungal
(74) *Attorney, Agent, or Firm* — QUARLES & BRADY LLP

(57) ABSTRACT

Exemplary method and apparatus for diagnosing or characterizing an inflammation within an anatomical structure can be provided. For example, using at least one source arrangement, it is possible to provide at least one first electromagnetic radiation to the anatomical structure at at least one first wavelength in vivo. With at least one detector arrangement, it is possible to detect at least one second electromagnetic radiation at at least one second wavelength provided from the anatomical structure. The second radiation can be associated with the first radiation, and the first wavelength can be shorter than the second wavelength. The second radiation can be provided from the anatomical struc-
(Continued)

ture due to at least one change in the anatomical structure caused by the inflammation without providing an artificial fluorescence substance. At least one computer arrangement can be used to determine at least one characteristic of the structure based on the second radiation to diagnose or characterize the inflammation within the anatomical structure.

24 Claims, 28 Drawing Sheets

Related U.S. Application Data

(60) Provisional application No. 62/029,007, filed on Jul. 25, 2014.

(51) Int. Cl.
| | | |
|---|---|---|
| *A61B 5/145* | (2006.01) | |
| *A61B 5/1459* | (2006.01) | |
| *A61B 6/03* | (2006.01) | |
| *A61B 6/00* | (2006.01) | |
| *A61B 5/02* | (2006.01) | |

(52) U.S. Cl.
CPC .......... *A61B 5/0084* (2013.01); *A61B 5/0086* (2013.01); *A61B 5/055* (2013.01); *A61B 5/1459* (2013.01); *A61B 5/14546* (2013.01); *A61B 6/032* (2013.01); *A61B 6/504* (2013.01); *A61B 5/02007* (2013.01); *A61B 5/7267* (2013.01)

(58) Field of Classification Search
CPC ... A61B 5/055; A61B 5/14546; A61B 5/1459; A61B 6/032; A61B 6/504; A61B 5/02007; A61B 5/7267; A61K 49/0004; G02B 6/036; G01N 2800/00
See application file for complete search history.

(56) References Cited

U.S. PATENT DOCUMENTS

| | | | |
|---|---|---|---|
| 7,697,975 | B2 | 4/2010 | Zeng |
| 9,498,136 | B2 * | 11/2016 | Lucassen ............ A61B 5/0091 |
| 2003/0055307 | A1 * | 3/2003 | Elmaleh ............... A61B 5/0086 600/1 |
| 2003/0236453 | A1 * | 12/2003 | Furnish .............. A61B 5/02007 600/341 |
| 2004/0268421 | A1 * | 12/2004 | Tearney .............. A61L 27/3625 800/9 |
| 2005/0075704 | A1 * | 4/2005 | Tu ........................ A61N 5/062 977/932 |
| 2007/0078348 | A1 * | 4/2007 | Holman ............. A61B 5/02007 600/476 |
| 2008/0013960 | A1 * | 1/2008 | Tearney ............. G02B 21/0064 398/139 |
| 2009/0018424 | A1 * | 1/2009 | Kamath ................. C12Q 1/006 600/347 |
| 2009/0131769 | A1 * | 5/2009 | Leach ................ A61B 5/14546 604/65 |
| 2009/0192358 | A1 * | 7/2009 | Jaffer .................... A61B 5/0073 600/182 |
| 2009/0253989 | A1 * | 10/2009 | Caplan ................ A61B 5/0086 600/587 |
| 2015/0148665 | A1 * | 5/2015 | Sato .................. A61M 39/0208 348/162 |

FOREIGN PATENT DOCUMENTS

| | | |
|---|---|---|
| JP | 2006081619 A | 3/2006 |
| WO | 2013152395 A1 | 10/2013 |

OTHER PUBLICATIONS

Japan Patent Office. Notice of Reasons for Rejection for application 2020-067787, dated May 11, 2021. With translation. 9 pages.
Japan Patent Office, Decision of Rejection, Application No. 2020-067787, dated Mar. 8, 2022, 4 pages.
Korean Intellectual Property Office, Notice of Final Rejection, Application No. 10-2017-7005420, dated Jul. 22, 2022, 11 pages.
Korean Intellectual Property Office, Notice of Allowance, Application No. 10-2017-7005420, dated Jan. 18, 2023, 5 pages.
Japan Patent Office, Trial and Appeal Decision, Appeal 2022-10668, Application No. 2020-067787, May 9, 2023, 38 pages.
Japan Patent Office, Notice of Reasons for Refusal, Application No. 2022-110132, dated May 16, 2023, 10 pages.

* cited by examiner

APPARATUS, DEVICES AND METHODS FOR IN VIVO IMAGING AND DIAGNOSIS

CROSS-REFERENCE TO RELATED APPLICATIONS

The present application is a continuation of U.S. patent application Ser. No. 15/327,801 filed Jan. 20, 2017, which is a national phase of International Patent Application No. PCT/US2015/042283 filed Jul. 27, 2015, which relate to and claims priority from U.S. Provisional Patent Application Ser. No. 62/029,007 filed Jul. 25, 2014, the disclosures of which are incorporated herein by reference in their entirety.

STATEMENT REGARDING FEDERALLY SPONSORED RESEARCH

This invention was made with government support under HL093717 awarded by the National Institutes of Health. The government has certain rights in the invention.

FIELD OF THE DISCLOSURE

The present disclosure relates to medical imaging, and more particularly to exemplary embodiments of apparatus, method and apparatus for imaging and diagnosis, and even more particularly, e.g., for molecular imaging of inflammation and oxidative stress by near infrared autofluorescence (NIRAF).

BACKGROUND INFORMATION

Molecular imaging is drawing research attention, which can reveal important molecular expressions in human body, such as, e.g., inflammation[1], oxidative stress (see, e.g., Ref. 2), cellular signalling pathway (see, e.g., Ref. 3), enzyme activities (see, e.g., Ref. 4)[2], etc. Molecular information can be important for the diagnosis of various diseases, such as cancer (see, e.g., Ref. 5), cardiovascular diseases (see, e.g., Ref 6), neurodegenerative diseases (see, e.g., Ref. 7) and ophthalmological diseases (see, e.g., Ref 8). Clinically used medical imaging tools such as Computed tomography (CT) (see, e.g., Refs. 9011), magnetic resonance imaging (MRI) (see, e.g., Refs. 12-16), ultrasound (IVUS) (see, e.g., Refs. 17 and 18), optical coherence tomography (OCT) (see, e.g., Refs. 19-22) can acquire morphological information of anatomical structures, but are limited to a detection of molecular information. As clinically used function imaging tools, positron emission tomography (PET) (see, e.g., Ref 23) and single-photon emission computed tomography (SPECT) (see, e.g., Ref 24) rely on medicinal radiopharmaceuticals, which are not aimed at detecting native molecular information of the anatomical structures either.

To image inflammation biomarkers on the tissue, e.g., exogenous reagents can be employed to label different cellular receptors and molecular species inside human body, such as blood stream and luminal organs. For example, near infrared fluorescent (NIRF) dyes are specifically designed to label cells, chemicals and enzymes associated with inflammation, such as macrophages (see, e.g., Ref. 25), fibrin (see, e.g., Ref. 26) and cysteine protease (see, e.g., Refs. 26 and 27). However, the toxicity, uptake and clearance of such reagents can cause high potential risk for the safety and health of patients. The regulatory approval of exogenous reagents can be time consuming and significantly inhibits the clinical application.

Endogenous imaging methods are also being investigated intensively, such as ultraviolet/visible autofluorescence (see, e.g., Refs. 18-31), time resolved fluorescence/fluorescence lifetime imaging (see, e.g., Refs. 32-32), near infrared spectroscopy (NIRS)/diffusive reflectance spectroscopy (see, e.g., Ref. 36-39), and Raman spectroscopy (see, e.g., Refs. 40-44). While these exemplary techniques can detect certain chemical information, such as, e.g., cholesterol, cholesterol ester, collagen, and elastin, they may not be sufficient to evaluate biomarkers of inflammation and oxidative stress. Therefore it is challenging to correlate the information provided by the above endogenous imaging modalities with inflammation and oxidative stress directly.

Accordingly, there may be a need to address and overcome at least such deficiencies described herein above. For example, this can be done, e.g., by providing another (e.g., label free molecular) imaging modality to detect an inflammation on the tissue.

SUMMARY OF EXEMPLARY EMBODIMENTS

To address and/or overcome the above-described problems and/or deficiencies, exemplary embodiments of device, method and apparatus to determine molecular information associated with important physiological events such as inflammation and oxidative stress using near-infrared autofluorescence (NIRAF). For example, such apparatus, device and method can be employed for detecting vulnerable atherosclerotic plaques using NIRAF.

According to an exemplary embodiment of the present disclosure, apparatus, devices and methods can be provided for detecting the presence of native autofluorescence from anatomical features that have been modified by naturally occurring oxidative processes within the body including the process of inflammation.

For example, autofluorescence excited using light or other electro-magnetic radiation, in the red and near-infrared region of the optical spectrum can be produced automatically in biological tissues or in the modification of biological tissues, where the modification can be a result of oxidative stress and inflammatory activity.

NIRAF can be generated by the optical absorption of light by biological tissues, which can then re-radiate the NIRAF light or other electro-magnetic radiation at a longer wavelength than the excitation light.

One of exemplary features of NIRAF is that the radiation/output used and/or produced thereby is provided in a wavelength region where hemoglobin and water have low molecular absorption cross sections.

This exemplary feature facilitates a deeper penetration of NIRAF excitation and better transmission of the returning NIRAF emission, and can reduce the risk for biological tissue damage.

Due to a low optical absorption by water and hemoglobin, the NIRAF spectrum may provide a low amount of wavelength-dependent attenuation. NIRAF signal levels can be directly correlated with concentration of the autofluorescence moiety. Additional exemplary procedures, apparatus, devices and methods required to correct for the wavelength-dependence of the absorption, such as diffuse reflectance spectroscopy, to recover the intrinsic NIRAF spectrum may not be required to produce a diagnostically valid result.

One exemplary feature of NIRAF is that a diagnostically valid result can be achieved without the requirement for multiwavelength detection and additional spectral processing methods.

An exemplary selection of NIRAF wavelength can reduce interfering fluorescence signals from structural proteins and other known biological autofluorescent molecules such as NADH and FAD. By using the exemplary NIRAF procedure, it is possible to detect atherosclerotic plaques containing necrotic material with high sensitivity and specificity against lipid-rich, e.g., that is not necrotic, and other atherosclerotic plaques.

One exemplary feature of the NIRAF signal is that the signal can be related to modifications of proteins and lipo-proteins through the mechanism of oxidative stress.

Dityrosine cross linkages can be one exemplary feature that can produce the NIRAF signal.

According to an exemplary embodiment of the present disclosure, the implementation of the exemplary NIRAF procedures, apparatus, devices and methods can be combined with other structural imaging modalities such as OCT, OFDI, SD-OCT, TD-OCT, SECM, SEE, photoacoustics, confocal endoscopy, ultrasound, angioscopy, bronchoscopy, colonoscopy, and eye-box. NIRAF data can be analyzed by intensity, spectral ratio, e.g., between 2 or more bands, principal component analysis, linear least squares, wavelets transformation, support vector machines and/or neural networks.

According to additional exemplary embodiments of the present disclosure, using the output of the NIRAF analysis, diagnostic predictions can be obtained using logistic regression, discriminant analysis, cluster analysis, factor analysis, and other supervised and unsupervised decision tools.

Thus, exemplary method and apparatus for diagnosing or characterizing an inflammation within an anatomical structure according to an exemplary embodiment of the present disclosure can be provided. For example, using at least one source arrangement, it is possible to provide at least one first electro-magnetic radiation to the anatomical structure at at least one first wavelength in vivo. With at least one detector arrangement, it is possible to detect at least one second electro-magnetic radiation at at least one second wavelength provided from the anatomical structure. The second radiation can be associated with the first radiation, and the first wavelength can be shorter than the second wavelength. The second radiation can be provided from the anatomical structure due to at least one change in the anatomical structure caused by the inflammation without providing an artificial fluorescence substance. At least one computer arrangement can be used to determine at least one characteristic of the structure based on the second radiation to diagnose or characterize the inflammation within the anatomical structure.

According to another exemplary embodiment of the present disclosure, apparatus and method can be provided. For example, a catheter can be configured and structured to be inserted into a blood vessel. With an energy source arrangement, it is possible to provide at least one first light radiation through the catheter to the blood vessel at at least one first wavelength. In addition, with a detector arrangement, it is possible to detect at least one second light radiation through the catheter at at least one second wavelength that is different from the first wavelength. The second light radiation can be based on an autofluorescence of at least one portion of the blood vessel being impacted by the at least one first light radiation. Further, with a computer arrangement, it is possible to determine at least one characteristic of the blood vessel based on the second light radiation to diagnose or characterize at least one characteristic of the blood vessel.

According to yet another exemplary embodiment of the present disclosure, apparatus and method can be provided.

For example, a catheter configured and structured to be inserted into a blood vessel. With an energy source arrangement, through the catheter, at least one first light radiation can be provided to the blood vessel at at least one first wavelength that is between 550 nm and 800 nm. With a detector arrangement, it is possible to detect, through the catheter, at least one second light radiation at at least one second wavelength that is between 640 nm and 900 nm. The second light radiation can be based on an autofluorescence of at least one portion of the blood vessel being impacted by the first light radiation. Further, with a computer arrangement, it is possible to determine at least one of oxidative stress, calcium, intraplaque hemorrhage, protein modification, lipo-protein modification, lipid modification, and/or enzymatic activity based on the second light radiation.

In another exemplary embodiment of the present disclosure, the first wavelength can be between 600 nm to 90 nm, between 600 and 800 nm, between 650 nm to 750 nm, and/or between 650 nm and 700 nm. The second wavelength can be between 640 nm and 1000 nm, and/or between 640 nm and 800 nm. The second wavelength can be selected to be outside a wavelength range of the background emission of a double clad fiber optic. An upper end of the wavelength range can be more than 20 nm or 40 nm. The second wavelength can be a plurality of second wavelengths, and the detection can be performed as a function of the second wavelengths. The detection can include a mathematical manipulation of an emission spectrum of the second radiation to further specify the characterization of the inflammation.

As indicated herein, the characteristic can be at least one of oxidative stress, calcium, intraplaque hemorrhage, protein modification, lipo-protein modification, lipid modification, and/or enzymatic activity. The protein modification can be dityrosine or nitrotyrosine, the lipo-protein modification can be oxidized LDL, the intraplaque hemorrhage can contain endogenous porphyrins. At least one third radiation can be provided to the sample and at least one fourth radiation to a reference. At least one fifth radiation that is an interference between the third and fourth radiations can be received, and the determination can be performed as a further function of the fifth radiation. The first radiation can be at least partially co-localized with the first radiation.

In a further exemplary embodiment of the present disclosure, wherein the structure can be a coronary artery. The first electro-magnetic can be provided within the coronary artery. The coronary artery can be in a patient suspected of having necrotic plaque.

According to a still further exemplary embodiment of the present disclosure, the determination can be performed by detecting at least two second wavelength ranges, characterizing a spectral shape data or a relative intensity data with the at least two second wavelength ranges, and comparing the spectral shape or relative intensity data to a training data set. The spectral shape data can be compared as a ratio of the second wavelength ranges. The spectral shape data or relative intensity data can be calibrated with noise or sensor parameters. The characterizing process can comprise analyzing with a principle component analysis method.

In yet another exemplary embodiment of the present disclosure, the determination can include detecting the plurality of second wavelengths, scoring a spectral shape and relative intensity with the second wavelengths, and comparing a third score to a training data set. Further, the second radiation can be provided in a first range that is between 640 nm and 600 nm and in a second range that is between 660 nm and 900 nm, and the determination can comprise comparing a ratio of the first and second range to a training data set.

According to yet another exemplary embodiment of the present disclosure, an apparatus and method can be provided. For example, with an energy source, it is possible to provide at least one first light radiation to a structure at at least one first wavelength. The wavelength can be controlled to be between 400 nm and 900 nm. With a detector arrangement, it is possible to detect at least one second light radiation at at least one second wavelength which is different from the first wavelength. The second light radiation can be based on an autofluorescence of at least one portion of the structure being impacted by the first light radiation. Further, with a computer arrangement, it is possible to generate at least one first image of the portion(s) of the structure and at least one gradient second image based on the second light radiation.

For example, the first or second images can be co-registered. The generation procedure can comprises obtaining an OCT image, an IVIS image, an angiographic image, a CT image, or an MRI image. The second image can include a display of a ratio of at least two wavelength ranges of the second light radiation.

In still a further exemplary embodiment of the present disclosure, an apparatus can be provided comprising a double clad fiber structure which is configured to facilitate at least one of an optical coherence tomography and/or NIR fluorescence and transmit a fluorescence signal. The double clad fiber structure can include at least one core and at least one cladding. A configuration of the core and the cladding can be is provided such that a ratio of the core to the cladding causes a reduction or a minimization of a bending loss of the fluorescence signal, and wherein the configuration further effectuates a reduction or a minimization of a background fluorescence. A computer can be provided which calibrates the fluorescence background signal based on the background fluorescence of the double clad fiber.

Exemplary embodiments of the present disclosure can be advantageous in that there is no need to add an exogenous label. Generally, with fluorescence detection, the addition of an artificial or exogenous fluorescent moiety may be required, which can increase the time and complexity of a diagnostic or therapeutic procedure. According to the exemplary embodiments of the present disclosure, the use of dityrosine or other fluorophores found in an anatomical structure can facilitate diagnosis or characterization without the need to add an exogenous fluorescent moiety into the anatomical structure.

These and other objects, features and advantages of the exemplary embodiments of the present disclosure can become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

Figure 1:
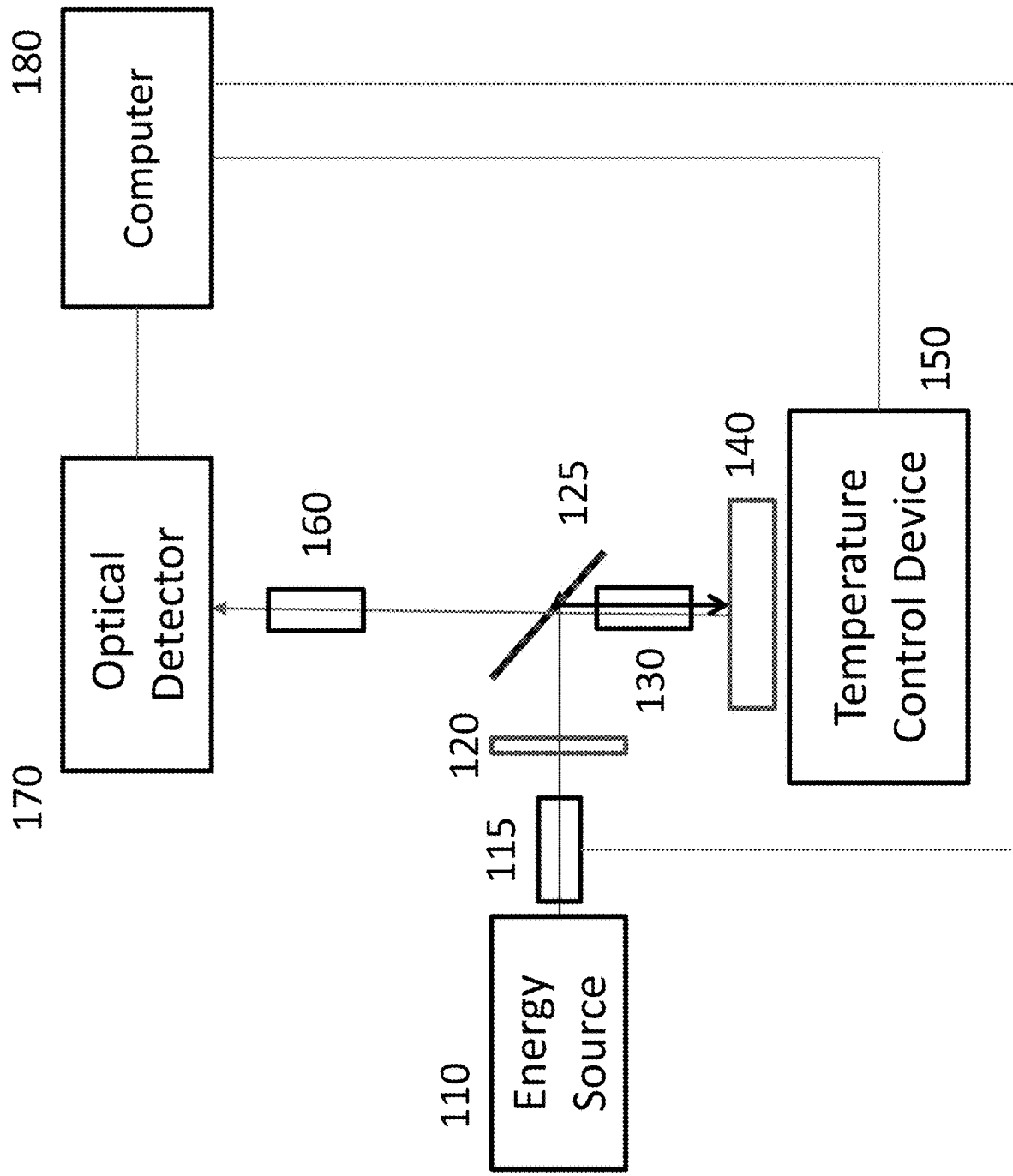
FIG. 1 is a schematic block diagram of an exemplary embodiment of a near-infrared (NIR) auto-fluorescence arrangement/system according to the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure and appended claims.

DETAILED DESCRIPTION OF EXEMPLARY EMBODIMENTS

Figure 2:
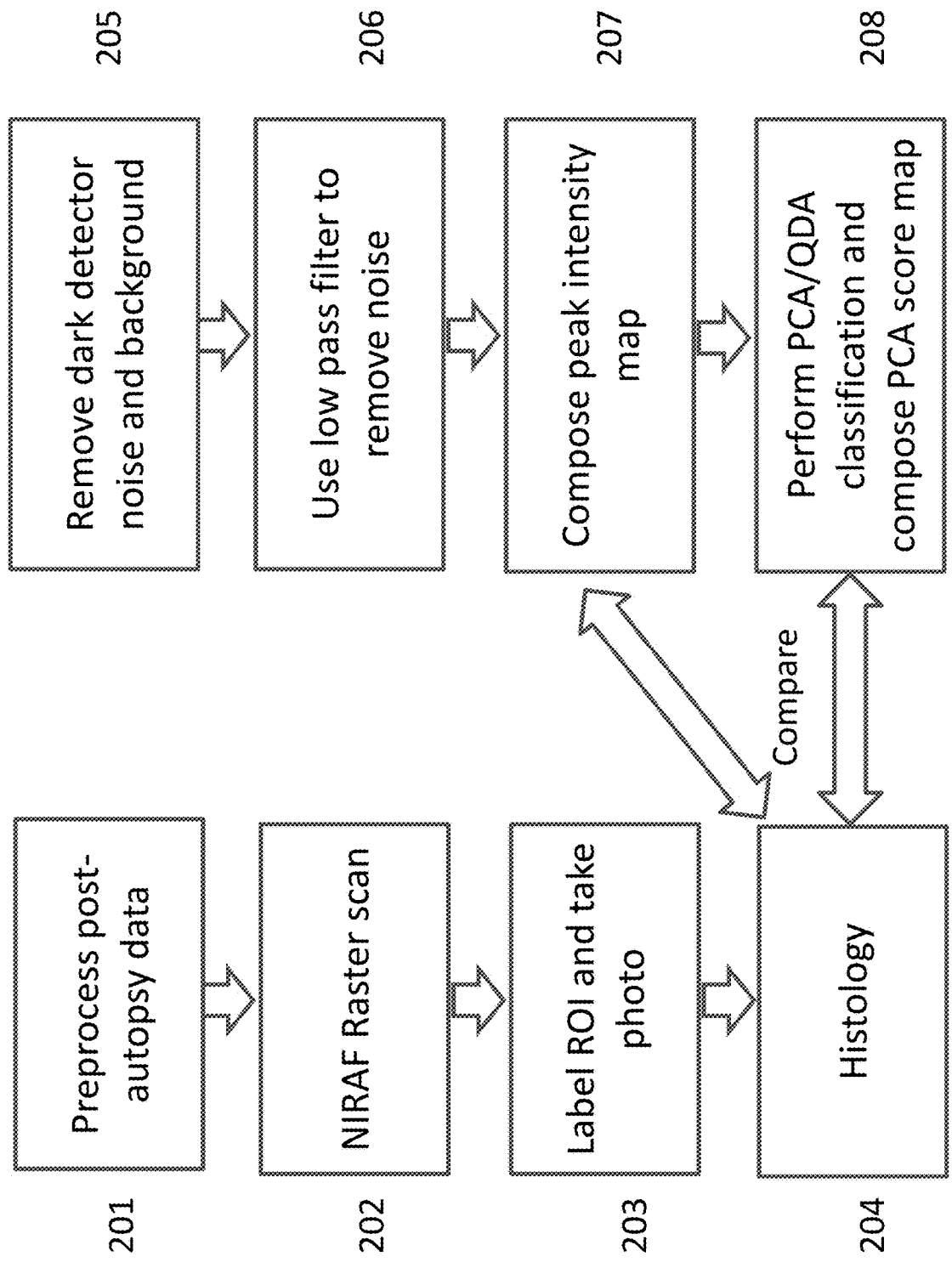
FIG. 2 is a flow diagram of an exemplary embodiment of the method to collect, process and analyze data according to the present disclosure.

As shown in a diagram of FIG. 1, the exemplary device according to an exemplary embodiment of the present disclosure can be composed an energy source, e.g., a narrow band (0.1 nm) diode laser 110 emitted light at an exemplary wavelength of 740 nm. A lens assembly 115 can be used to produce collimated light that can be passed through a short pass filter 120 to remove spurious emission from the laser source, reflected off a dichroic beam splitter filter 125 and focused by a second lens assembly 130 onto the arterial specimen or another sample 140. The arterial specimen is mounted on a computer controlled three-dimensional stage with a temperature control device 150. The emitted light from the arterial specimen 140 is collected by the same lens assembly 130 in, e.g., a 180 degree backscattering geometry and approximately collimated, transmitted through a dichroic beamsplitter 125, focused by a second lens assembly 160, which contains a long pass filter. The assembly 160 focuses the emitted light into an optical detector 170. A computer 180 (e.g., an exemplary embodiment of which is illustrated in a block diagram of FIG. 27) can control the motion of the stage and operation of the energy source 110, and can acquire and/or process the NIRAF signal. It should be understood that the tissue/sample described herein can include various anatomical structures and/or biological tissues such as, e.g., arterial tissue, blood vessels FIG. 2 shows a flow diagram of an exemplary embodiment of the method according to the present disclosure for data collection and processing, which can be implemented by the computer 180 shown in FIGS. 1 and 27. In particular, the exemplary method can be provided for collecting NIR auto-fluorescence and OFDI datasets. In general, fiduciary marks can be placed at corners or the auto-fluorescence scan indicating the region of interest (ROI) after scanning the tissue. OFDI beam is aligned with the ROI and scanned. Standard data processing methods/procedures can be employed to condition the auto-fluorescence signal. NIRAF spectra are acquired from the luminal side in bulk measurement and unless otherwise noted in the text. For example, according to the exemplary embodiment shown in FIG. 2, post-autopsy data can be obtained and pre-process (procedure 201). Then, OFDI beam can be aligned, and NIRAF Raster scan performed (procedure 202). ROI can be labeled and an image/photograph taken (procedure 203). Histology can be performed (procedure 204). Further, dark detector noise and background can be removed (procedure 205), and noise can be removed, e.g., using a low pass filter (procedure 206). Peak intensity map can be generated (procedure 207) which can work in conjunction or together with the histology (procedure 204). Further. Principal component analysis and quadrant discrimination analysis (PCA/QDA) qualification can be performed, and PCA map can be formed (procedure 208), and compared to the histology.

Figure 3:
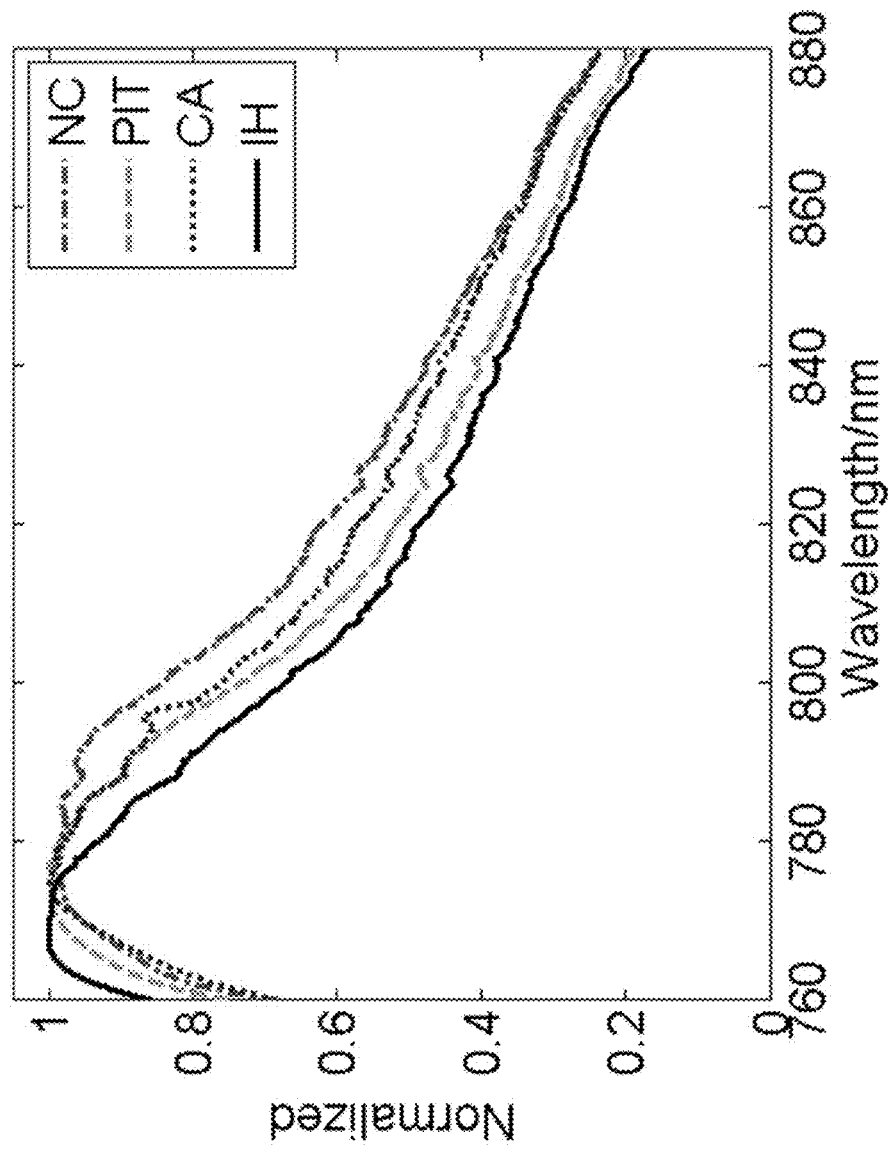
FIG. 3 is a graph of exemplary autofluorescence spectra of the present disclosure acquired by an exemplary NIRAF apparatus/system shown in FIG. 1.
Figure 4:
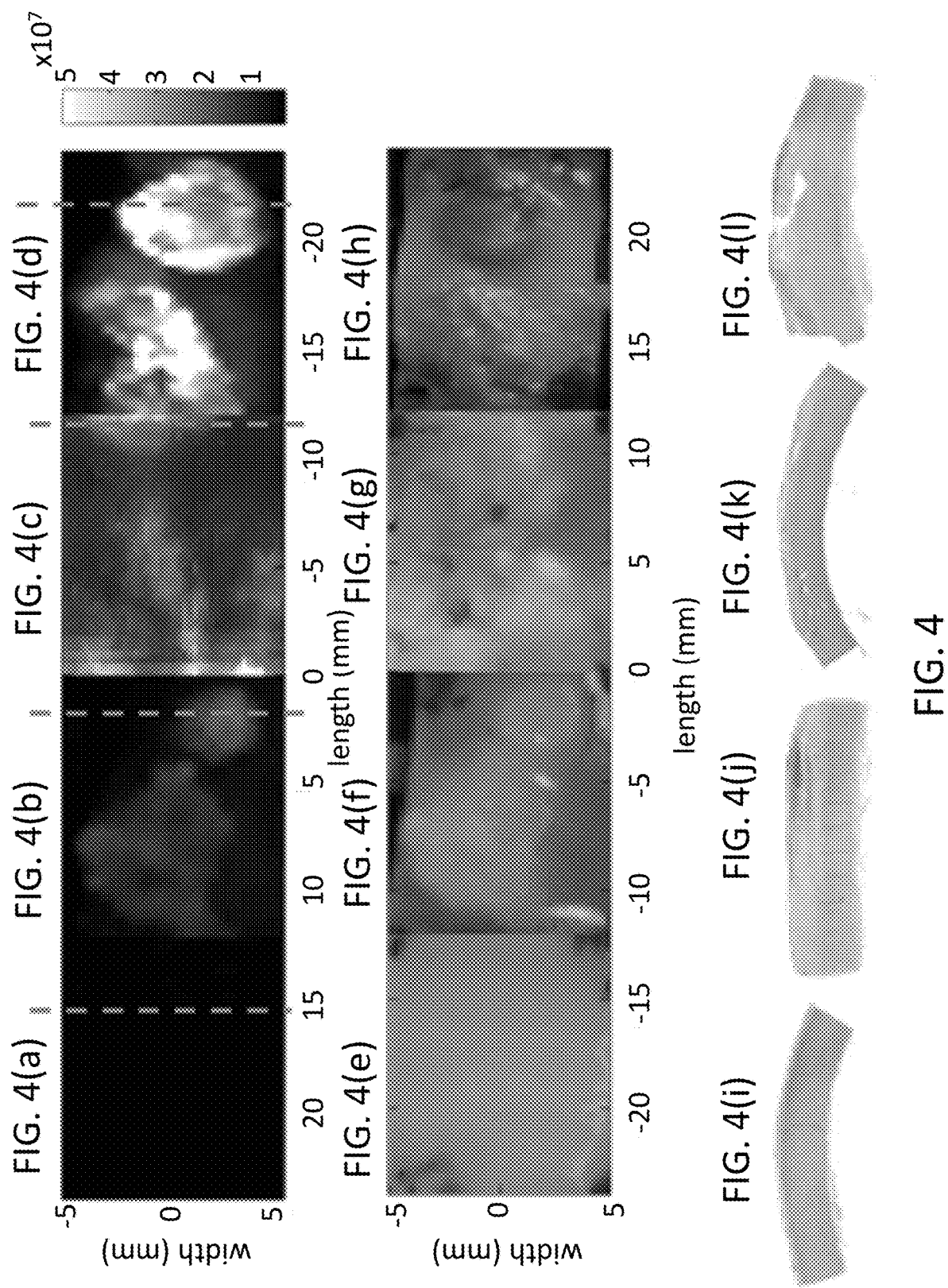
FIGS. 4(a)-4(l) is a set of illustrations of comparisons of gross pathology (FIGS. 4(a)-4(d)) and associated NIRAF map (FIGS. 4(i)-4(l)) from four representative plaques, using the exemplary embodiments of apparatus, device and method according to the present disclosure.

FIG. 3 shows a graph of representative exemplary autofluorescence spectra obtained from different atherosclerotic pathologies using the apparatus, device and method according to exemplary embodiments of the present disclosure. The representative spectra, which are normalized to the maximum intensity, can be obtained from specific sites located in intimal hyperplasia (IH), calcified (CA), pathological intimal thickening (PIT) and necrotic core (NC) plaques. Normalized spectra can illustrate a difference in spectral shape in the 760-820 nm region, which can indicate an exemplary change in the molecular composition between plaque types.

FIGS. 4(a)-4(l) shows a set of illustrations comparing the gross pathology (top row—FIGS. 4(a)-4(d)) and associated NIRAF map (middle row—FIGS. 4(e)-4(h)) to the preferable standard histology (bottom row FIGS. 4(i)-4(l)) from 4 representative plaques, using the apparatus, device and method according to the exemplary embodiments according to the present disclosure. For example, NIRAF intensity maps can be normalized to maximum intensity for the dataset. The following exemplary figures correspond to pathologies provided in this figure: intimal hyperplasia (see FIGS. 4(a), 4(e), 4(i)); fibrocalcific plaque (see FIGS. 4(b), 4(f), and 4(j)); pathological intimal thickening (see FIGS. 4(c), 4(g), 4(k)); necrotic core (see FIGS. 4(d), 4(h), 4(l)). These exemplary plaques can be diagnosed by histology.

Figure 5:
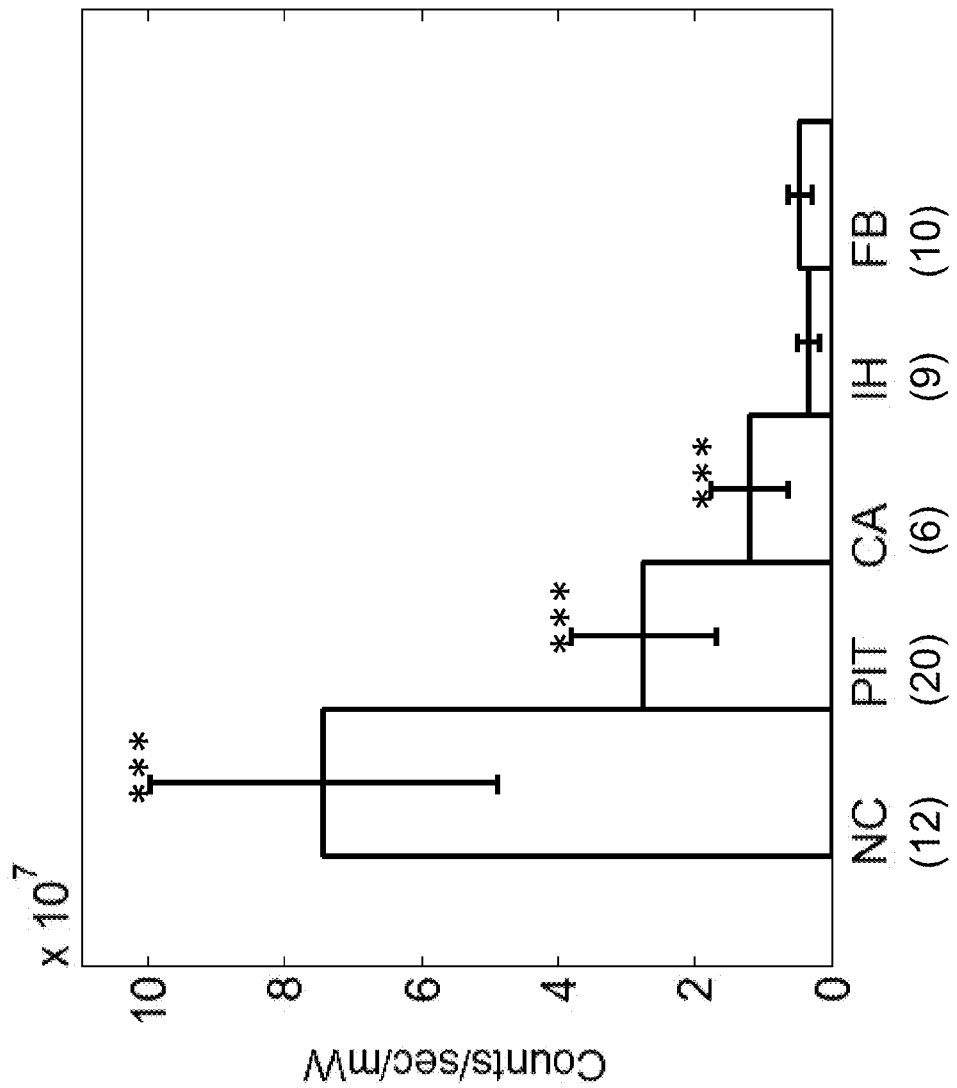
FIG. 5 is an graph providing an exemplary comparison of NIRAF intensity collected from 67 atherosclerotic plaques.

FIG. 5 illustrates an exemplary graph providing an exemplary comparison of NIRAF intensity among 67 plaques. For example, in this graph, there are 13 necrotic core plaques, 21 pathological intimal thickening, 10 fibrocalcific plaques, 9 intimal hyperplasia plaques, and 14 fibrous plaques. Using one way analysis of variance (ANOVA), the NIRAF intensities of NC, PIT and CA can be significantly different from IH and FB (p<0.0001). This can mean that NIRAF can differentiate different types of plaques based on intensity information.

Figure 6A:
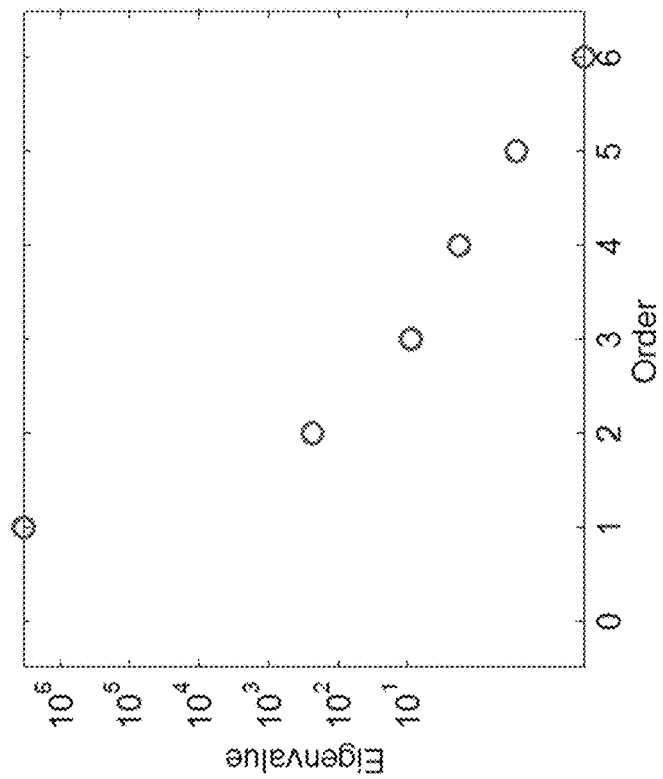
FIG. 6(a)-6(b) are graphs providing exemplary results from a principal component analysis of NIRAF spectra acquired from 67 atherosclerotic plaques.
Figure 6B:
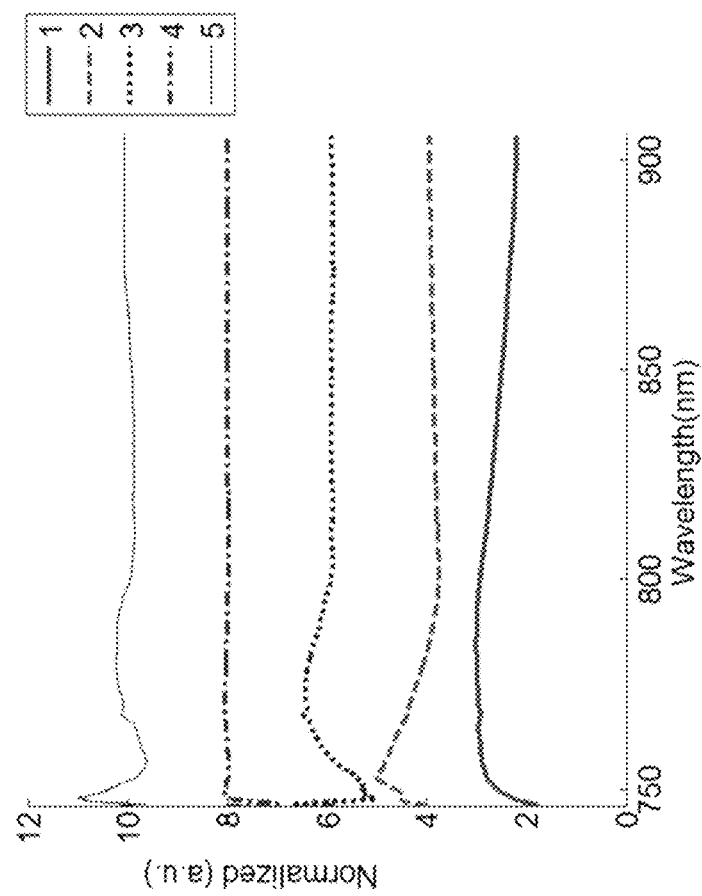

FIGS. 6(a) and 6(b) shows exemplary results obtained by applying principal component analysis (PCA) to a data set composed of 67 plaques according to exemplary embodiment of the present disclosure. In this example, autofluorescence spectra are preprocessed through normalization based on peak intensity (other normalization metrics may be employed) and then mean centered before applying the standard PCA algorithm/procedure with the specially-programmed computer (e.g., computer 180). Exemplary outputs of the PCA algorithm/procedure are the PCA scores (see FIG. 6(a)) and loading vectors or principal components (see FIG. 6(b)). In this example, the first two principal components or loading vectors can account for over 98% of the spectral variance. The second principal component illustrates an exemplary feature between about 760 nm and 820 nm, which likely agrees with the exemplary spectral shape variation.

Figure 7:
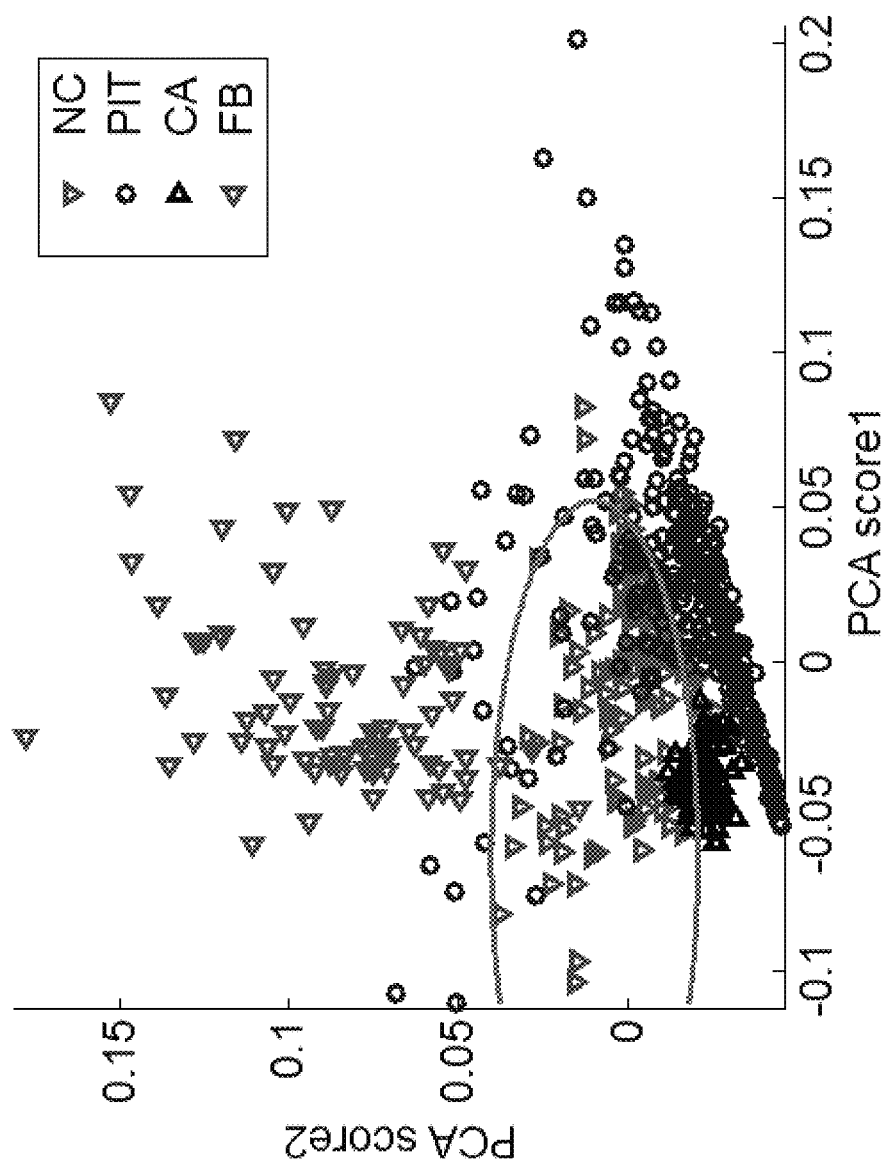
FIG. 7 is scatter plot illustrating an exemplary pathological classification scheme based on principal component analysis of all pathologies acquired from 67 atherosclerotic plaques.

FIG. 7 shows an exemplary scatter plot based on 1st and 2nd PCA scores provided using the apparatus, device and method according to the exemplary embodiments of the present disclosure, along with a table providing the exemplary results. For example, each type of plaques can have a specific distribution. Using the quadrant discrimination analysis (QDA), e.g., the PCA score plane can be divided into, e.g., four subspaces, representing four different categories: NC/PIT/CA/IH. Following an exemplary leave-one-out strategy, the sensitivity and specificity can be analyzed to differentiate plaque types. See Table 1 below for exemplary results.

TABLE 1

PCA-QDA classification of 4 plaque types

| Training set | NC | PIT | CA | FB | Sensitivity | Specificity |
|---|---|---|---|---|---|---|
| NC(128 sites) | 102 | 14 | 8 | 4 | 79.76% | 95.06% |
| PIT(332 sites) | 49 | 264 | 3 | 16 | 79.50% | 81.32% |
| CA(84 sites) | 0 | 1 | 83 | 0 | 98.81% | 99.8% |
| FB(84 sites) | 2 | 0 | 0 | 82 | 97.62% | 99.6% |

Figure 8:
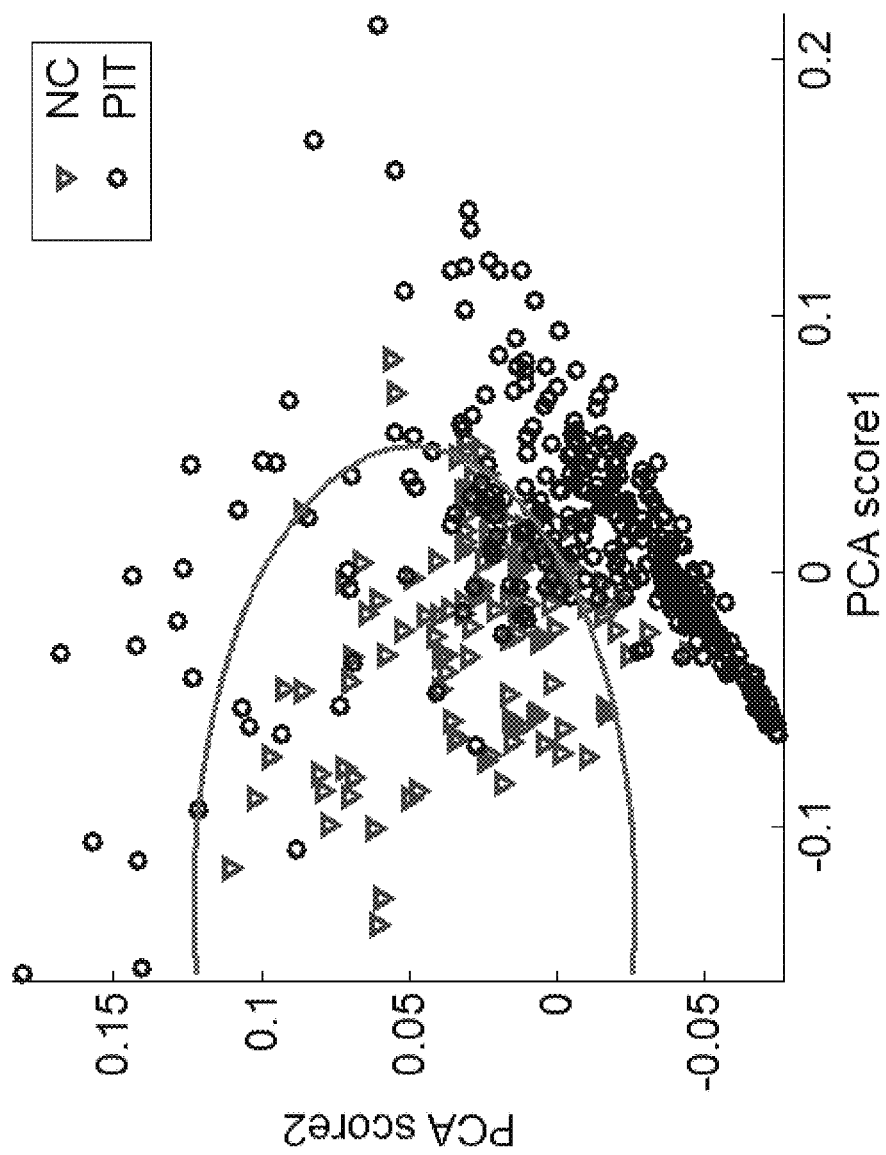
FIG. 8 is a scatter plot illustrating the discrimination between necrotic core and pathological intimal thickening pathologies classified by principal component analysis using discriminant analysis to construct the decision line, using the exemplary embodiments of the present disclosure.

FIG. 8 illustrates another exemplary scatter plot based on first and second exemplary PCA scores providing differentiated necrotic core from pathological intimal thickening provided using the apparatus, device and method according to the exemplary embodiments of the present disclosure, along with a table providing the exemplary results. For example, the overall exemplary accuracy can be about 85%. This analysis may demonstrate diagnostic value to utilize NIRAF spectra to not only detect lipid rich plaques, but also evaluate their risk potential. In other words, this NIRAF analysis appears more sensitive to differentiation of necrotic core plaques than stable lipid rich plaques such as pathological intimal thickening and fatty streak than other exemplary spectroscopic based technologies. See Table 2 below for exemplary results.

TABLE 2

PCA-QDA classification of NC and PIT

| Training set | Classified as PIT | Classified as NC | Result |
|---|---|---|---|
| PIT(332 sites) | 281 | 51 | SP = 84.6% |
| NC(128 sites) | 19 | 109 | SE = 85.2% |

Figure 9:
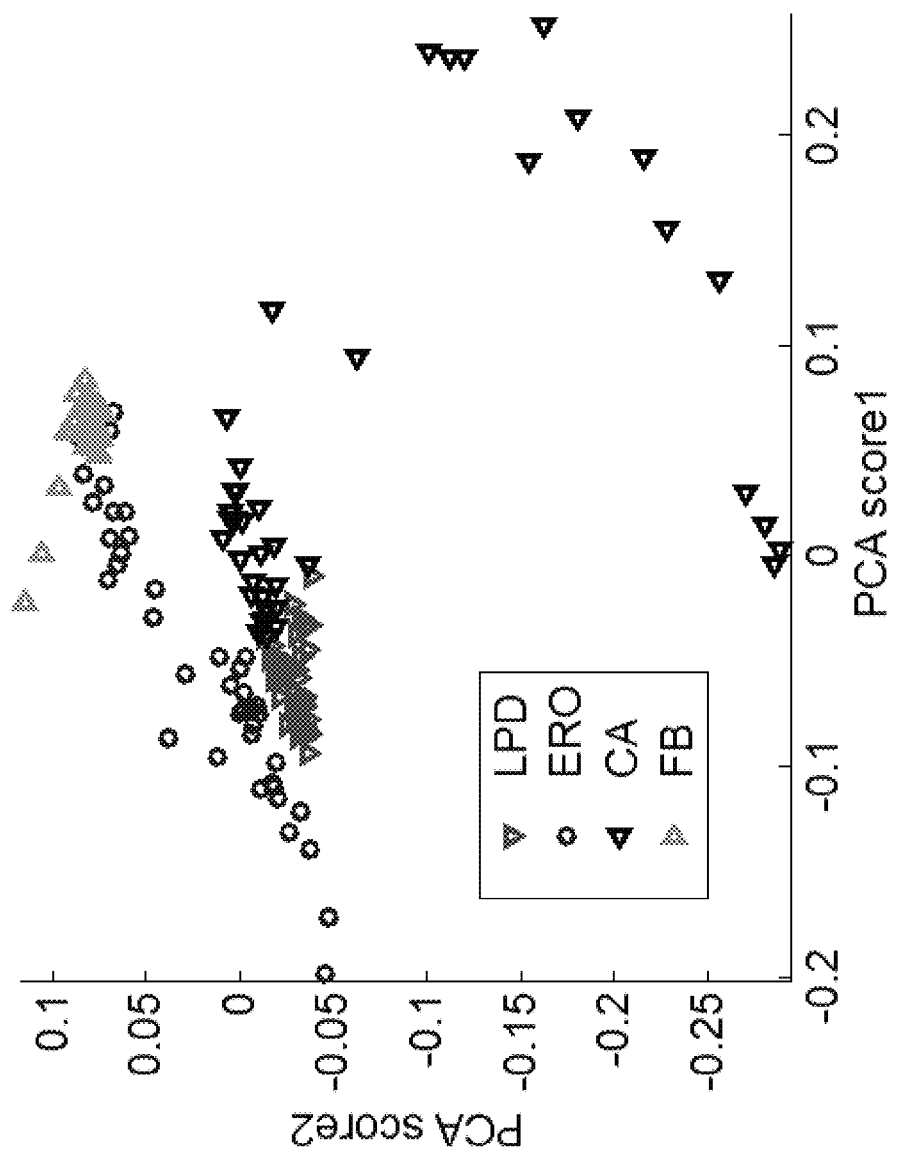
FIG. 9 is another scatter plot illustrating an exemplary pathological classification based applying principal component analysis applied to exemplary simulated spectral data at lower spectral using the exemplary embodiments of the present disclosure.

FIG. 9 shows an another exemplary scatter plot based on 1st and 2nd PCA scores of exemplary spectra data with reduced spectral resolution provided using the apparatus, device and method according to the exemplary embodiments of the present disclosure, along with a table providing the exemplary results. For example, each type of plaques can have a specific distribution. Using a quadrant discrimination analysis (QDA), the PCA score plane can be divided into, e.g., four subspaces, representing four different categories: lipid (LPD)/erosion (ERO)/calcification (CA)/fibrous (FB). Following an exemplary leave-one-out strategy, the sensitivity and specificity can be analyzed to differentiate plaque types. The results can show that the detected integrated spectral bandwidth of each channel can vary between 0.1 nm to 10 nm without loss of diagnostic capability. See Table 3 below for exemplary results.

TABLE 3

PCA-QDA based on multichannel PMT

|  | LPD | ERO | CA | FB |
|---|---|---|---|---|
| LPD | 39 | 0 | 1 | 0 |
| ERO | 0 | 35 | 1 | 4 |
| CA | 9 | 0 | 31 | 0 |
| FB | 0 | 0 | 1 | 39 |

Figure 10:
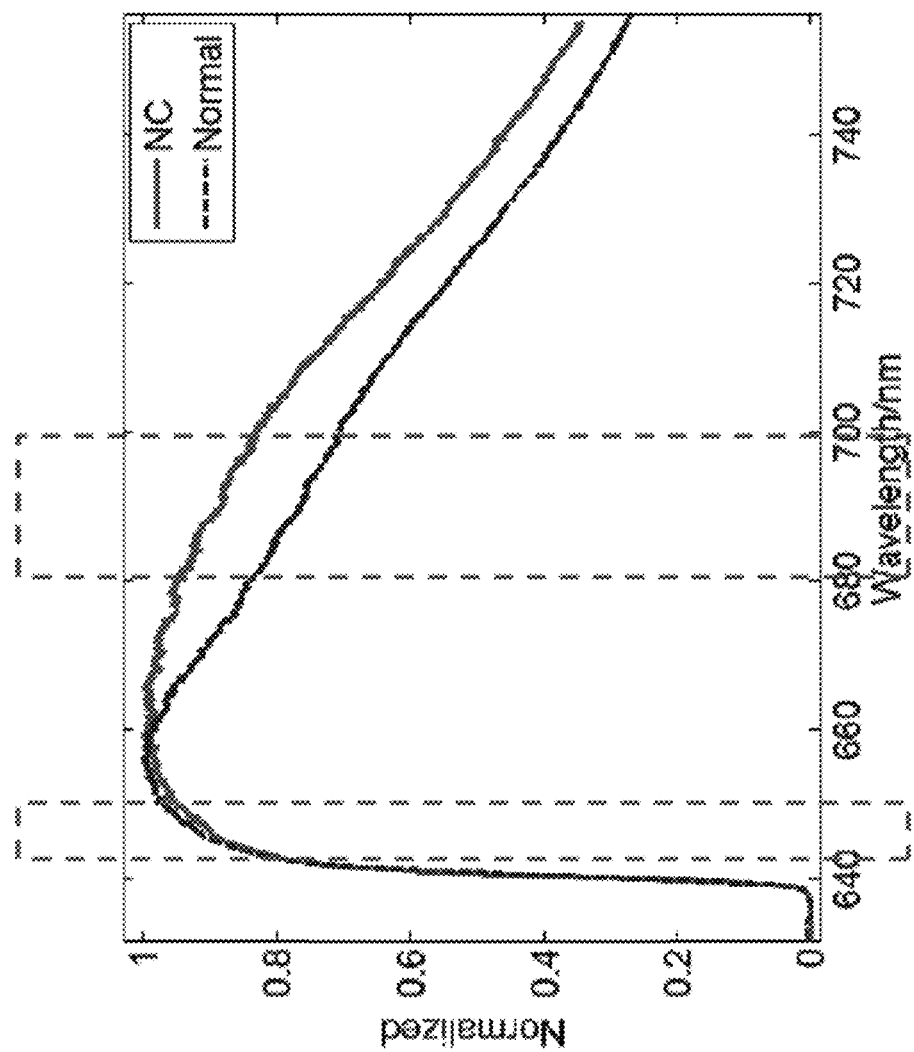
FIG. 10 is a graph illustrating the position of the spectral band relative to the exemplary autofluorescence spectra obtained from plaques classified as necrotic core and pathological intimal thickening.

A spectral band ratio can provide an exemplary method to monitor the changes in a set of NIRAF spectra without the requirement of spectral or statistical models. The spectral band ratio is constructed by integrating the intensity received in one spectral band having a defined spectral range by the integrated intensity of a second spectral band with its unique spectral range. FIG. 10 shows a graph illustrating the exemplary spectral integration regions compared to exemplary NIRAF spectra from representative necrotic core (NC) and pathological intimal thickening (PIT) plaques. In this example, the shorter wavelength band (blue channel) spans the wavelength region of 642-650 nm and the longer wavelength band (red channel) spans the region between 680-700 nm. The integrated signals from each exemplary spectral band can be divided to construct a spectral ratio, which can provide another example of the diagnostic contrast.

Figure 11:
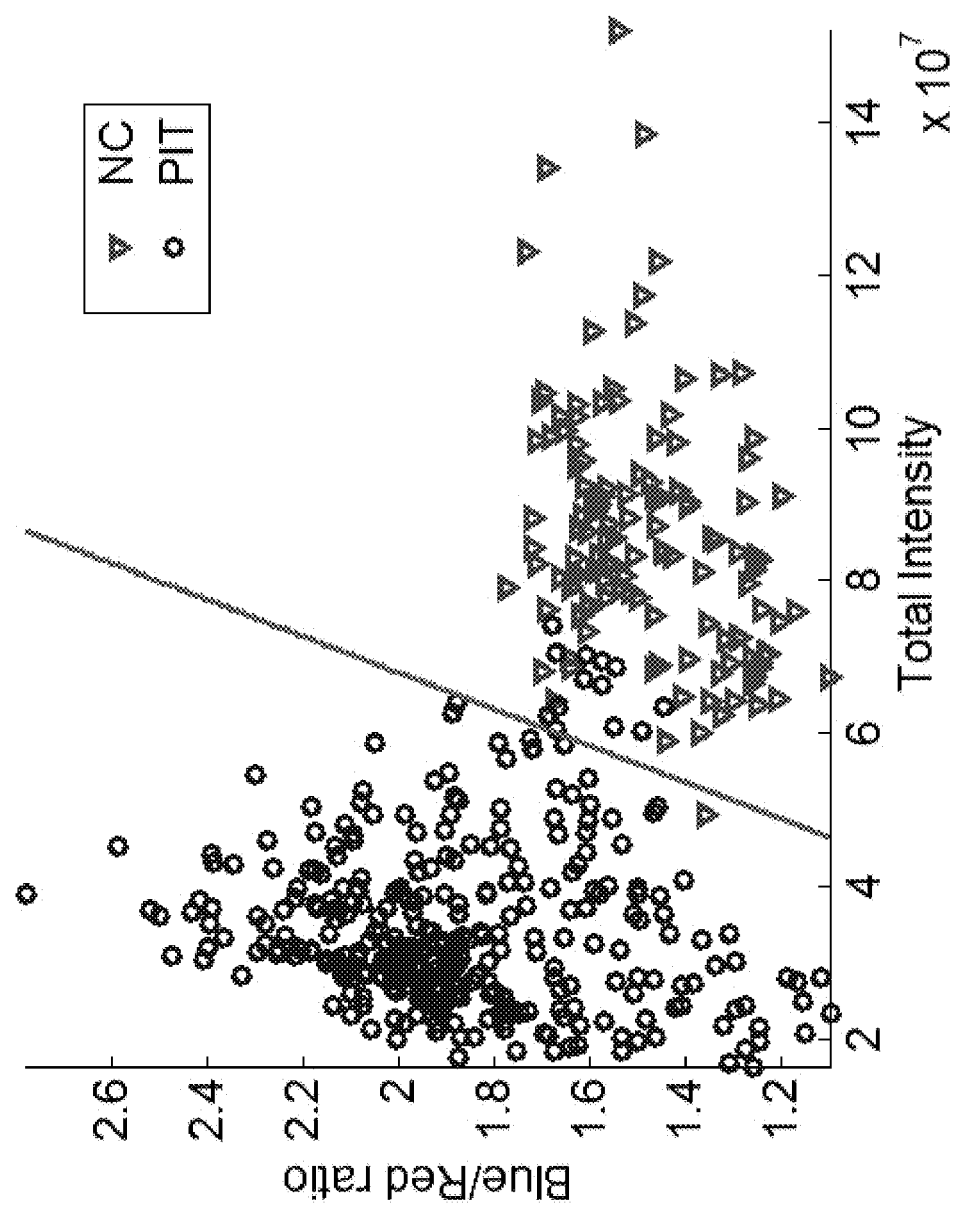
FIG. 11 is another scatter plot illustrating another pathological classification scheme based on ratioing integrated spectral band intensities using the exemplary embodiments of the present disclosure.

The spectral parameters that can be used to define the spectral bands can be optimized to provide the most sensitive diagnostic criteria based on changes in the spectra based on pathological state, presence of spectral interferents and background emission. FIG. 11 shows a scatter plot illustrating an exemplary diagnostic algorithm based a comparison of the integrated spectral intensity and the spectral ratio provided using the apparatus, device and method according to the exemplary embodiments of the present disclosure, along with a table providing the exemplary results. For example, a linear discriminant analysis can be applied to generate a decision line that can discriminate between necrotic core and pathological intimal thickening pathologies. The exemplary results show that the spectral parameters that define the blue and red bands discriminate between NC and PIT pathologies with high sensitivity and specificity. See Table 4 below for exemplary results.

TABLE 4

Double channel classification

| Training set | Classified as NC | Classified as PIT | Parameters |
|---|---|---|---|
| NC(128) | 127 | 1 | SE = 99.2% |
| PTT(332) | 14 | 318 | SP = 95.7% |
| Total (460) | 141 | 319 | Accuracy = 97.46% |

Figure 12:
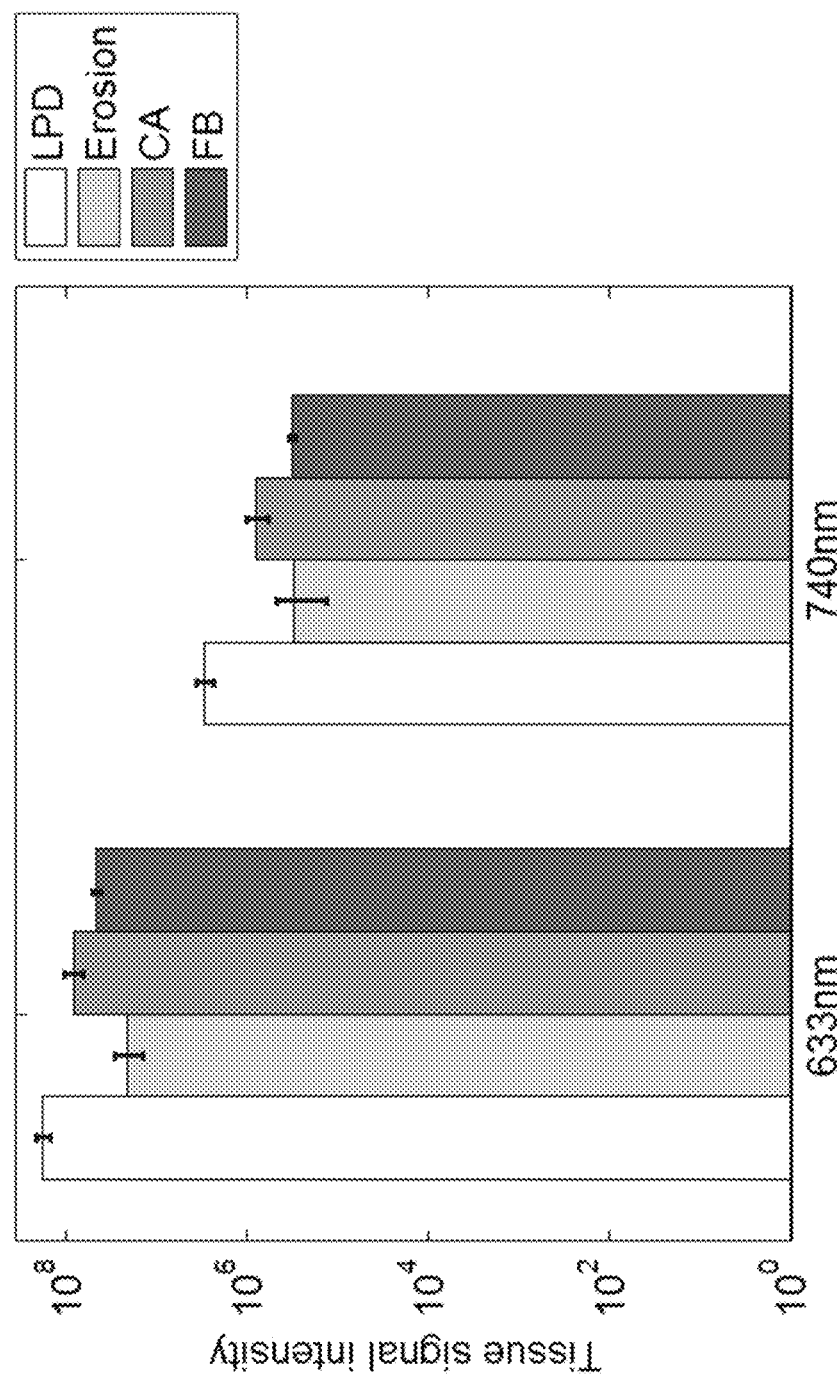
FIG. 12 is a graph illustrating the exemplary NIRAF signals levels for different pathologies at two exemplary excitation wavelengths, using the exemplary embodiments of the present disclosure.

Different excitation wavelengths in the near-infrared region can be used to generate autofluorescence spectra whose spectral properties can be used to discriminate between different atherosclerotic plaques. For example, FIG. 12 shows a graph evaluating the exemplary tissue signal levels between two exemplary excitation wavelengths at 633 nm and 740 nm using the apparatus, device and method according to the exemplary embodiments of the present disclosure. In FIG. 12, the Y-axis is provided in logarithmic scale. In this exemplary comparison of excitation-dependent signal strengths, the autofluorescence emission intensities have been normalized by the wavelength-dependent spectral response of the spectrometer and detector. Both excitation wavelengths illustrate similar NIRAF contrast among plaques. In addition, excitation light at 633 nm can provide stronger exemplary tissue signal levels.

The excitation wavelength (first light radiation or first electro-magnetic radiation) which can be used to diagnose or characterize inflammation can be, for example, between 600 nm and 900 nm, or between 600 nm and 850 nm, or between 620 nm and 770 nm, or between 630 nm and 750 nm, or between 650 nm and 700 nm. In other embodiments the first wavelength is between 400 and 600 nm or between 550 and 600 nm. This wavelength can be selected, for example, where the absorption difference between necrotic core and normal tissue is large or at an absorption peak of the necrotic tissue. For some embodiments, the excitation wavelength may be selected based on the absorbance of a different indicator tissue, such as pathological intimal thickening tissue.

The wavelength being detected (e.g., the second light radiation, or second electro-magnetic radiation) is selected to, for example, optimize the diagnostically relevant emission from the autofluorescent moiety and minimize background radiation-both from the tissue and from the fiber optics. An exemplary emission has a wavelength range from 640 nm to 1000 nm, up to 900 nm, or up to 800 nm. In some embodiments, the second light radiation has a wavelength range from 640 nm to 800 nm or from 680 to 770 nm. The 1000 nm upper limit is based on the sensitivity of the Si based detectors and can be extended, for example, with the use of InGaS-based detectors. Thus, for other detectors, a different upper limit may be indicated. In some embodiments the second light radiation is selected to have a range of wavelengths that is greater than 20 nm or greater than 40 nm. In some other embodiments, the second light radiation is selected to have two, three, or more ranges of wavelengths. In some embodiments, the second light radiation is selected to omit the local minima of the Si background. For example, the second light radiation may be selected so as to exclude the wavelengths at and around 600 $cm^{-1}$ and/or 800 $cm^{-1}$.

Figure 13A:
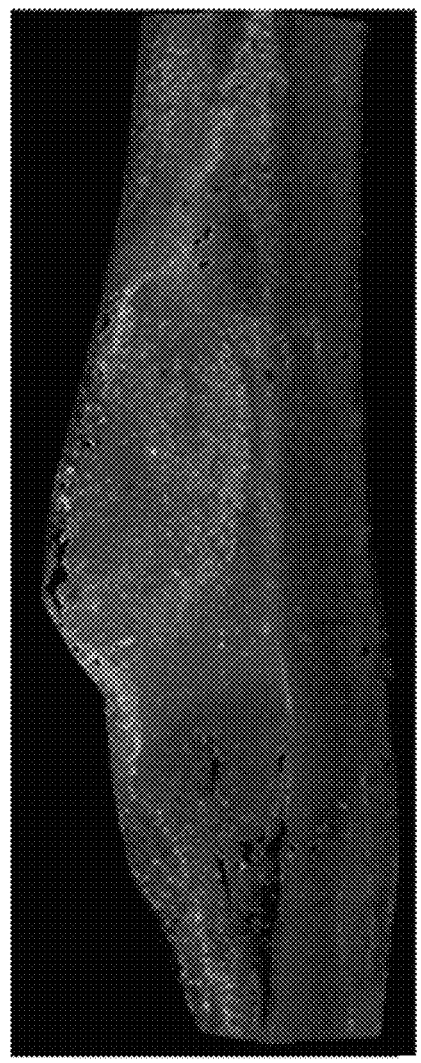
FIG. 13(a)-13(b) are images of the exemplary NIRAF and histological data obtained from a fresh, unfixed thin-section using the exemplary embodiments of the present disclosure.
Figure 13B:
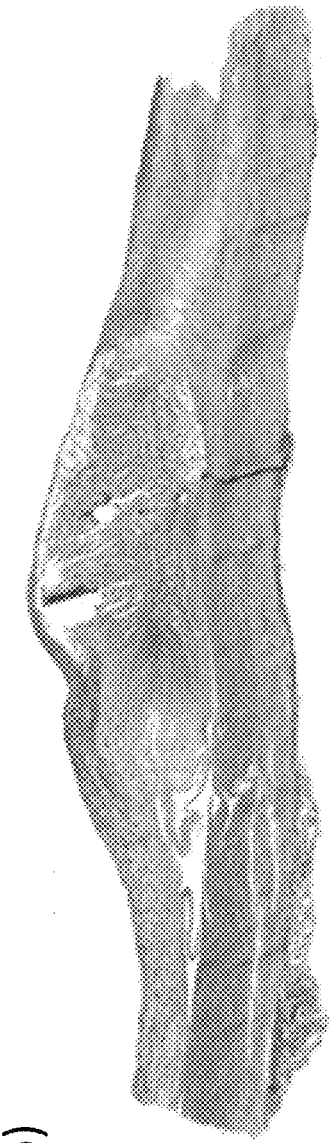
Figure 13:

NIRAF imaging can also be performed on histological thin-sections cut from fresh, unfixed arterial tissue whose thickness can be between approximately 5-10 μm. FIGS. 13(a) and 13(b) show an exemplary image and an exemplary NIRAF integrated intensity map, respectively, generated using the apparatus, device and method according to the exemplary embodiments of the present disclosure and a serially-cut thin-section that has been stained with a standard histology stain, such as Trichrome. The exemplary NIRAF map is displayed in a linear grey scale where regions of high spectral intensity appear white. Exemplary NIRAF imaging allows autofluorescence spectra to be obtained from specific morphological features. Registration between the NIRAF map and stained histology can allow spectral properties to be assigned to specific morphological features, such as the thin-fibrous cap, necrotic core region, foam cells, macrophages, neutrophils, collagen and elastin fibers, cholesterol clefts, calcification and ceroid deposits. The region of high spectral intensity is assigned to the necrotic region of a necrotic core plaque confirming that the autofluorescence observed from bulk tissue measurements is generated in the necrotic region where there are well established molecular-levels process responding to the inflammation and oxidative stress, such as modifications of proteins and lipids.

Figure 14A:
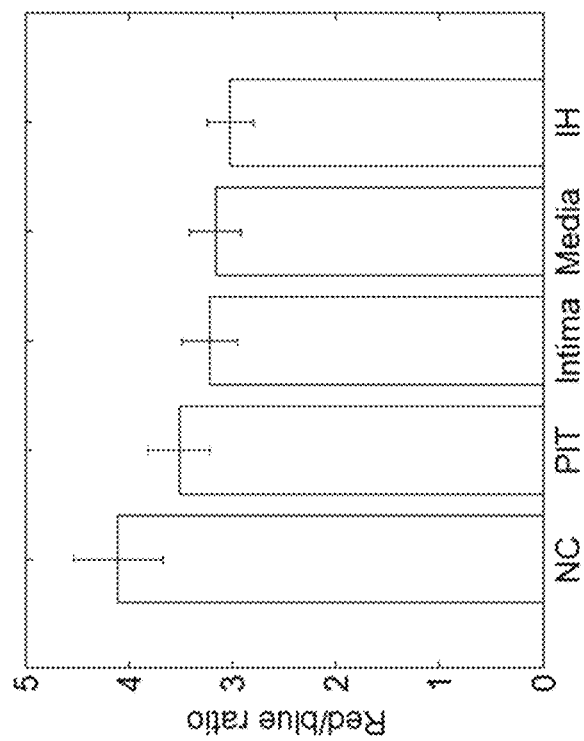
FIG. 14(a)-14(b) are graphs illustrating the integrated signal and spectral ratio levels acquired from representative atherosclerotic plaques obtained from fresh, unfixed aortic thin-sections with correlated pathologies using the exemplary embodiments of the present disclosure.

FIG. 14(a) shows a graph of the spectral band ratio that can be generated, according to an exemplary embodiment of the present disclosure, from the analysis of the analysis of 16 thin sections of differing pathologies. The error bar is one standard deviation, where NC—nectroic core, PIT—pathological intimal thickening, IH—whole intimal hyperplasia and the intima and media regions can be reported from PIT and NC plaques. Using one-way ANOVA, the intensity rank from high to low is NC>Media>IH≈PIT>Intima. Although NC is very heterogeneous, its intensity is significantly higher than the other four categories (p<0.01). Media has the second highest intensity, which is probably due to densely aligned elastin and smooth muscle fibers. Extracellular lipid pool has similar NIRAF intensity to the intima and IH, which suggests that lipid deposition by itself does not contribute to NIRAF.

Figure 14B:
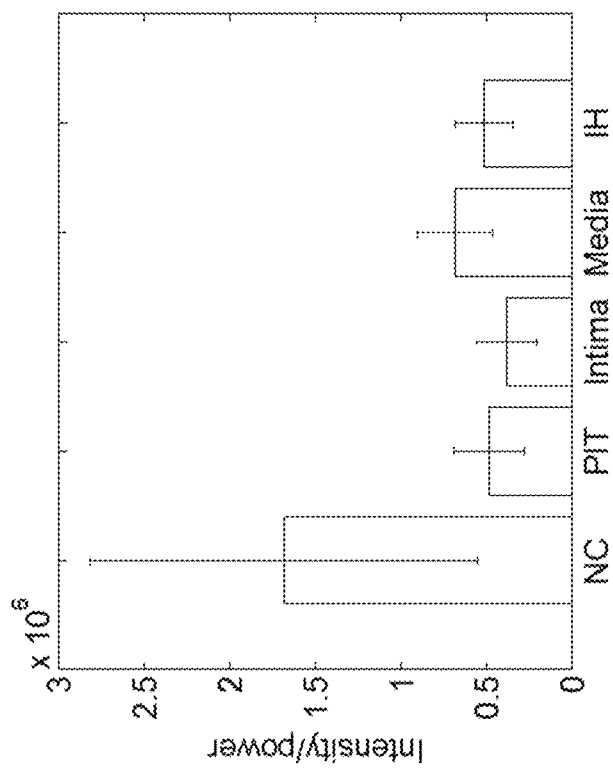

FIG. 14(b) shows a graph of the spectral band ratio, which can be used by an exemplary method to assess the difference in spectral shape between different morphological features. For example, the spectral ratio (blue/red) rank from high to low can be NC>PIT>Intima≈Media>1H. NC shows significantly stronger red shift than the other four categories (p<0.01). This agrees with observation from bulk tissue measurement. PIT has the second strongest red/blue ratio, which suggests that, as a transition between normal tissue and NC, PIT experiences certain chemical reactions and physiological processes, which lead to the generation of NIRAF fluorophore. Intima and media has similar red/blue ratio, which agrees with the fact that they both have collagen and elastin as main components. IH is slightly lower than intima/media of plaques. A possible reason can be that the inflammatory activities present in NC and PIT might modify proteins and lipo-proteins in the intima and media.

Figure 15B:
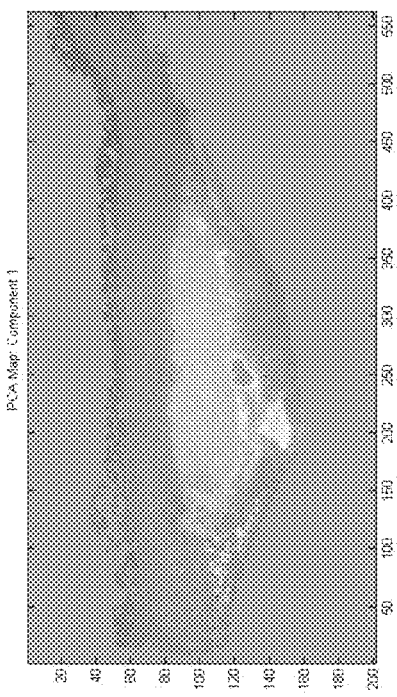
FIG. 15(a)-15(d) are images illustrating the integrated intensity and principal component scores for the first three principal components obtained from fresh, unfixed aortic thin-sections using the exemplary embodiments of the present disclosure.
Figure 15D:
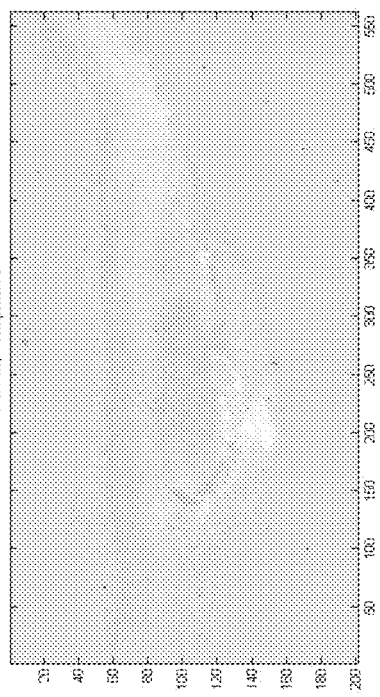
Figure 15A:
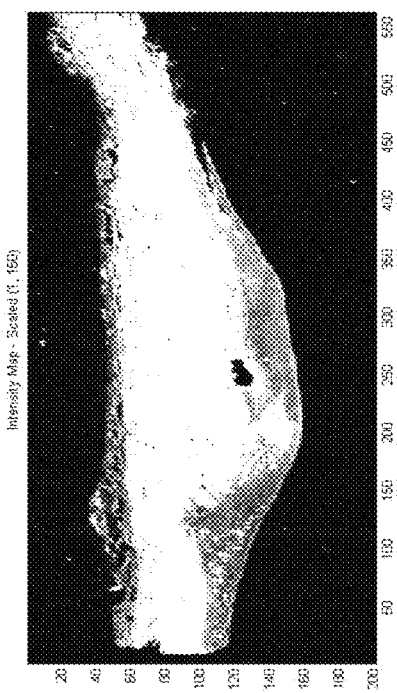
Figure 15C:
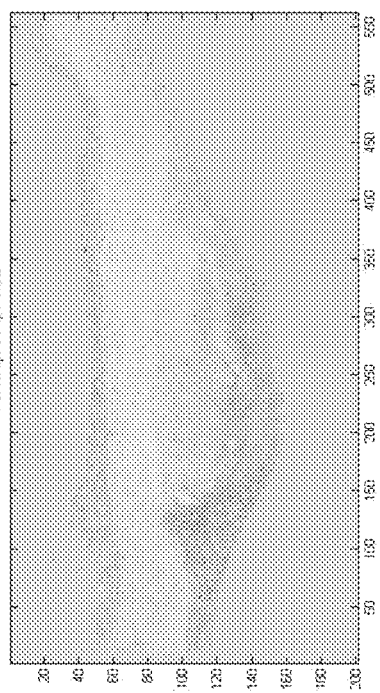

FIGS. 15(a)-15(d) show a set of images illustrating exemplary results obtained by performing principal component analysis on all autofluorescence spectra collected from a thin-section of a necrotic core plaque using the apparatus, device and method according to the exemplary embodiment of the present disclosure. The exemplary thin-section was cut from frozen tissue without formalin fixation or paraffin embedding. Autofluorescence spectra were acquired using the exemplary embodiments according to the present disclosure. Spectra were background subtracted, normalized by length of the vector prior to applying the PCA algorithm. For example, FIG. 15(a) is constructed from integrated spectra intensity and can show high intensity located in regions of both the necrotic core and media. The remaining images are constructed from the scores resulting from the first three principal components. The exemplary image in FIG. 15(b) is based on scores derived from the first principal component. This exemplary image can clearly outline the necrotic core region and can also show focal high intensity regions. For example, the first principal component accounts for over about 95% of the spectral variation. For comparison, PCA images based on the second and third components, shown in FIG. 15(c) and FIG. 15(d) respectively, can also highlight spectral differences and together account for approximately 3% of the spectral variation. The PCA-derived images highlight morphological regions that can be related to variations in the molecular compositional unlike the intensity based image.

Figure 16B:
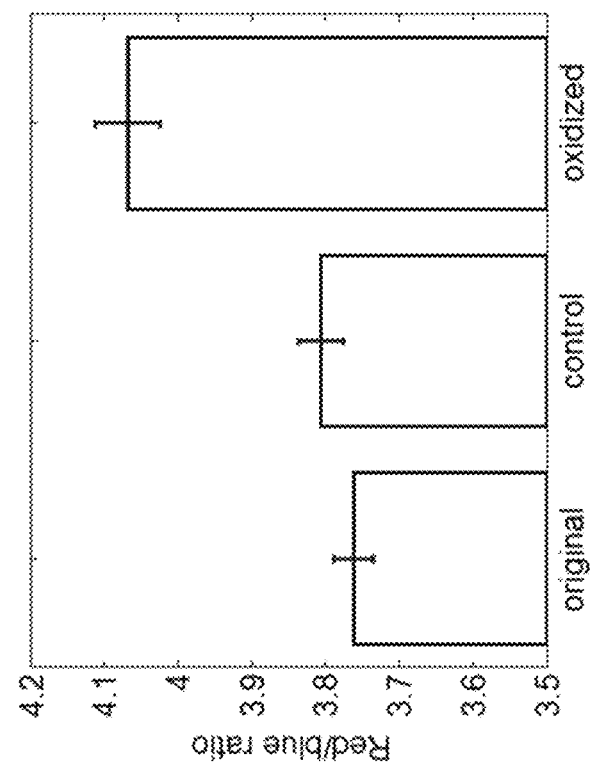
FIG. 16(a)-16(b) are graphs illustrating the exemplary spectral changes to the autofluorescence when human aortic tissue is exposed to an oxidizing agent.
Figure 16A:
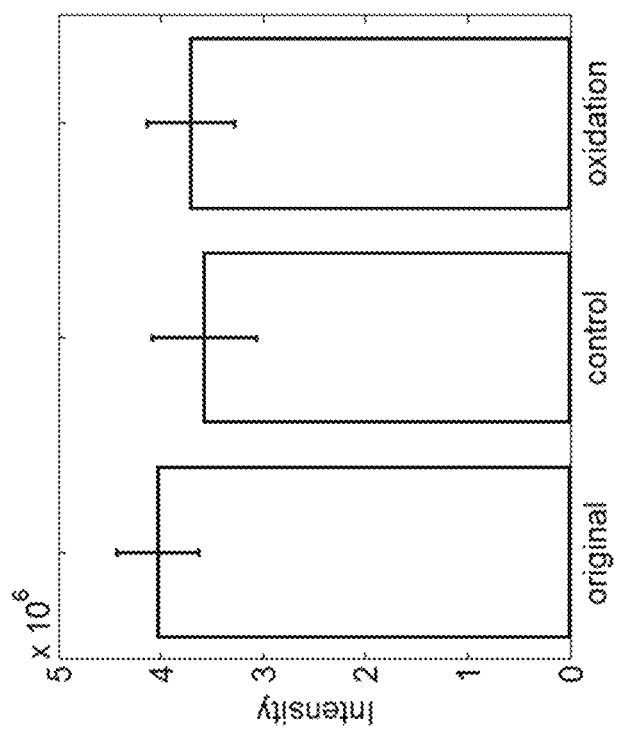

FIGS. 16(a)-16(b) show a set of graphs that illustrate the exemplary changes to the autofluorescence spectral properties generated using the apparatus, device and method according to the exemplary embodiments of the present disclosure. For example, an exemplary undiseased human arterial section can be evenly divided into two halves where one half is incubated at approximately 37° C. for over 12 hours in 10% phosphate buffered saline solution and where the second half is also incubated at the same temperature for the same time in an oxidative solution composed of saturated manganese (III) acetate dissolved in 10% phosphate buffered saline solution. The NIRAF spectra of the specimens were collected prior to incubation (original) and after incubation (control and oxidized). NIRAF integrated intensities are compared in FIG. 16(a) where the error bar indicates one standard deviation. The intensity of the original is not homogenous as indicated in FIG. 16(a). The intensity of the oxidized tissue exposed to manganese (III) acetate can be slightly higher than the control illustrating that the tissue autofluorescence can be increased by oxidizing agents that modify proteins. NIRAF spectral ratios are also compared in FIG. 16(b). The exemplary spectral ratio constructed as red/blue shift illustrates the expected red-shift in the autofluorescence spectra of the oxidized relative to the control tissue. The fact that control sample presents a small spectral red shift suggests minor tissue degradation or oxidation occurs during the incubation period. However, the sample incubated in saturated manganese (III) acetate solution shows significantly stronger spectral red shift. This demonstrates that the NIRAF spectral properties can be sensitive to the presence of oxidation products like protein modifications.

Figure 17A:
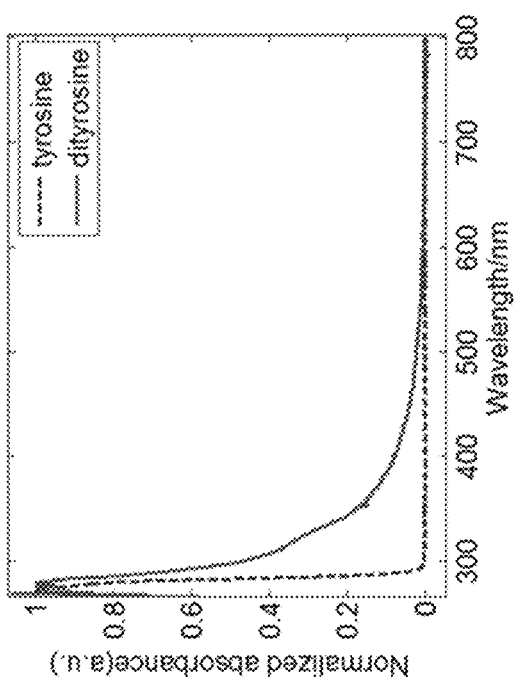
FIG. 17(a)-17(b) are graphs showing the exemplary spectral absorption and emission differences of dityrosine, an strongly autofluorescent biomarker of protein modification and oxidative stress.
Figure 17B:
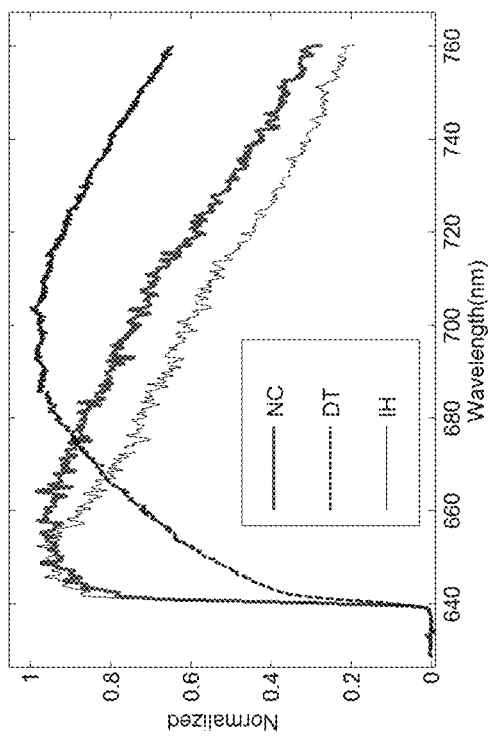

Dityrosine crosslinks are one of the well-established endogenous biomarker for protein modifications and emits a strong autofluorescence. FIGS. 17(a)-17(b) show a set of graphs that illustrate the absorption and autofluorescence spectral differences of dityrosine compared to tyrosine and human atherosclerotic plaques. For example, dityrosine has a maximum absorption at 280 nm and can have significant absorption through the visible region where as tyrosine is limited to the UV absorption (FIG. 17(a)). When excited at an exemplary excitation wavelength of 633 nm, fluorescence from dityrosine and autofluorescence from exemplary necrotic core (NC) and intimal hyperplasia (IH) plaques can be compared in FIG. 17(b). The dityrosine spectrum appears significantly red-shifted and can account for the red-shifted emission than can be seen as atherosclerosis progresses.

In addition to dityrosine crosslinks, additional morphological/histological structures such as fibrin, fibrinogen, lipofuscin, ceroid can also generate NIRAF signals. Well known oxidative products, such as chlorotyrosine, nitrotyrosine, bilirubin, biliverdin, 4-hydroxy-2-nonenal, hydroxyiminiodihydropyrrole, and porphyrins, can contribute to the NIRAF signal.

Figure 18:
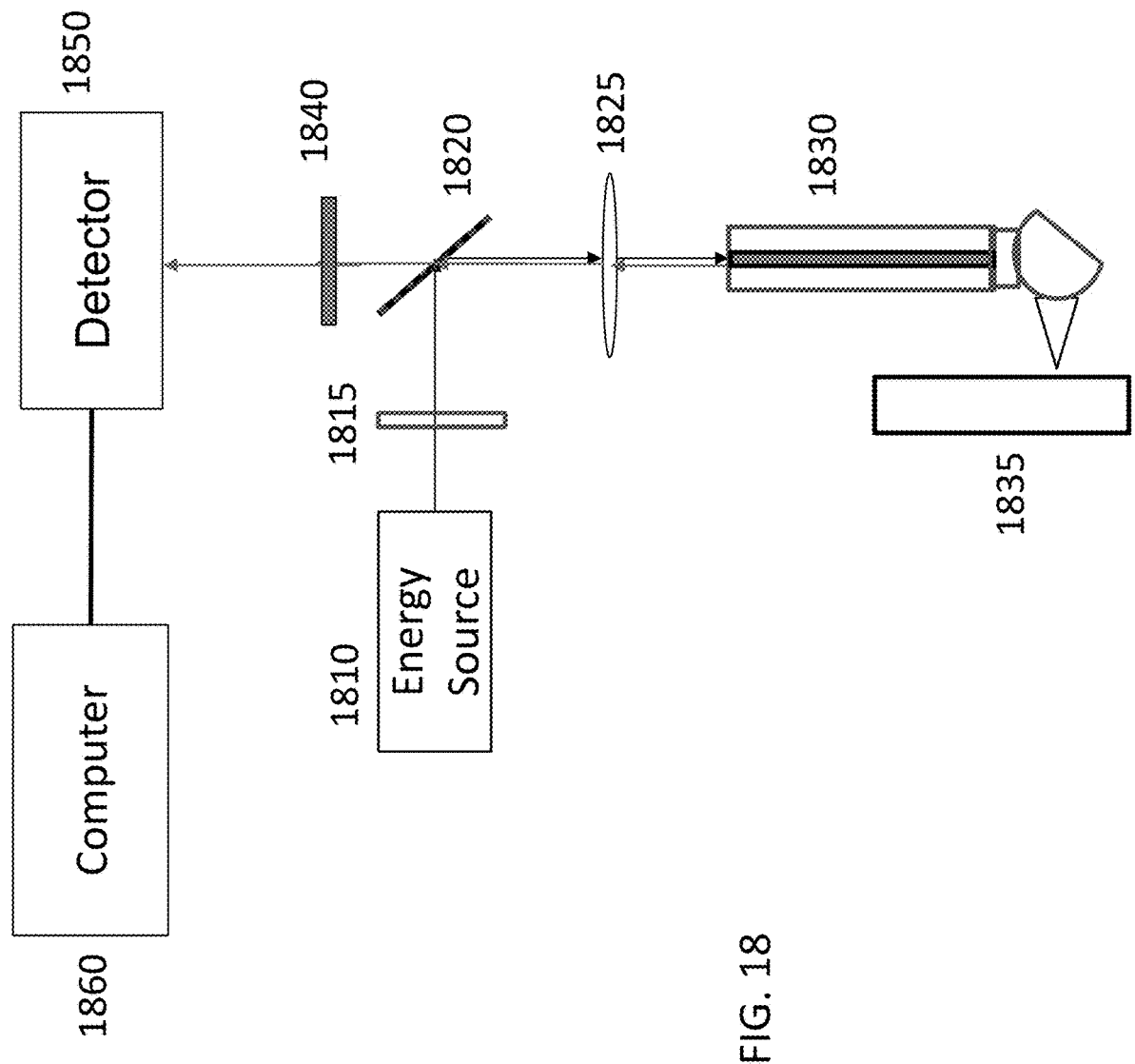
FIG. 18 is a schematic block diagram of the exemplary device/system/apparatus according to yet another exemplary embodiment of the present disclosure.

As shown in a diagram of FIG. 18, the exemplary device according to an exemplary embodiment of the present disclosure can be used to test dual clad fibers according to another exemplary embodiment of the present disclosure. This exemplary device/system shown in FIG. 18 can include an energy/light/laser source 1810, which can be or include, e.g., a narrow band (0.1 nm) diode laser emitting light at an exemplary wavelength of, e.g., about 633 nm produced, e.g., by a helium:neon laser or another light source. Collimated light from the source 1810 can pass through a short pass filter 1815 to remove spurious emission from the laser source, reflected off a dichroic beamsplitter filter 1820 and focused by a lens assembly 1825 into a double clad fiber ball lens probe 1830. The back reflected and fiber-generated fluorescence can be collected by the same lens 1830 in, e.g., a 180 degree backscattering geometry and collimated, filtered by the dichroic beam splitter 1820 and long pass filter 1840 and is focused into a detector 1850, which can be a single channel detector, an array of detectors, and/or an f/2 NIR spectrometer equipped with a low-light level CCD. Computer control can be accomplished using a computer 1860, which can be the a specially-programmed computer described herein.

Figure 19A:
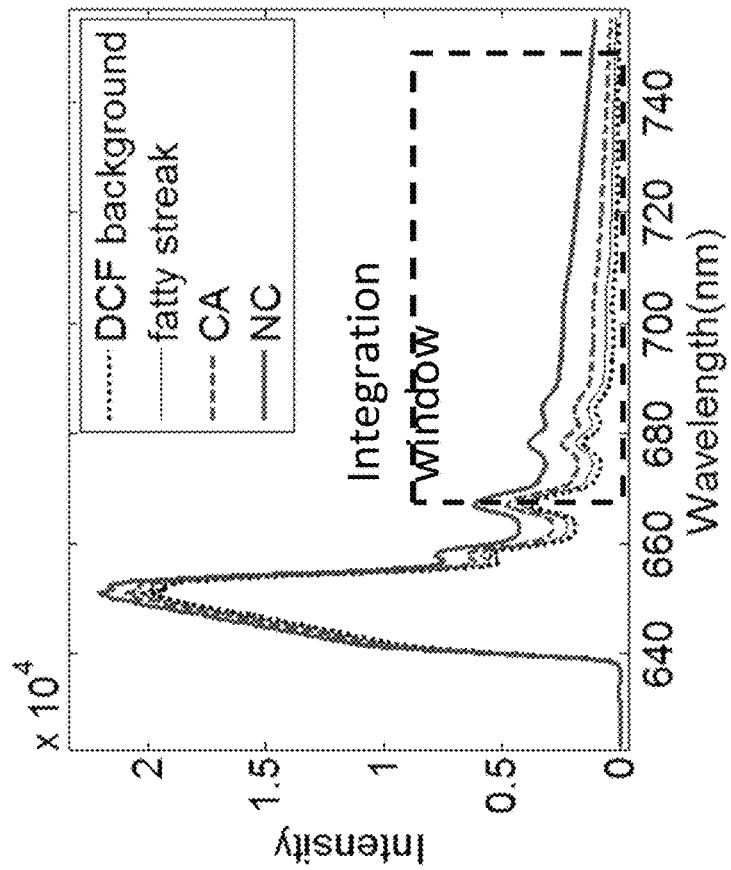
FIG. 19(a)-19(b) is a set of graphs illustrating an exemplary measurement of NIRAF spectra from lipid rich plaques, calcified plaques and fatty streak through a ball lens probe according to the exemplary embodiment of the present disclosure.
Figure 19B:
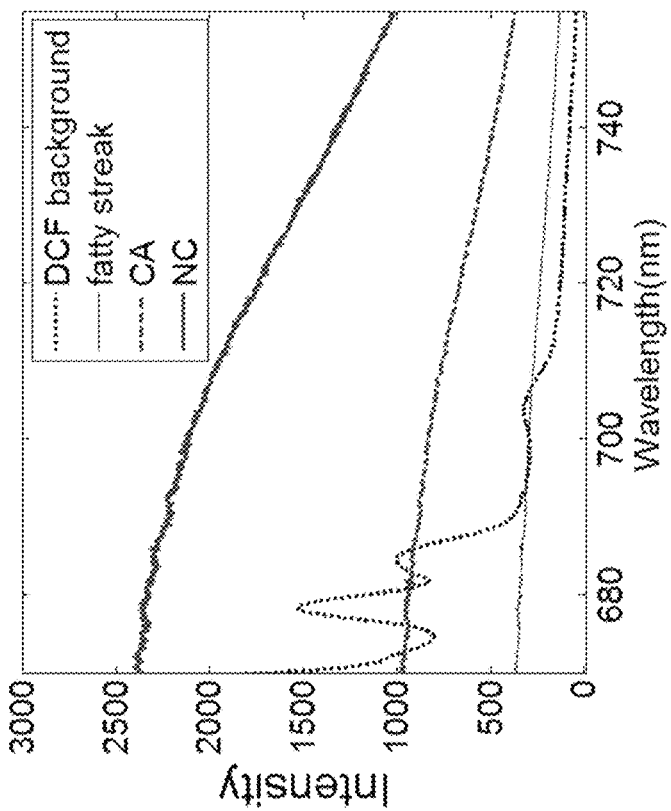

FIGS. 19(a)-19(b) shows a set of graphs illustrating an exemplary measurement of NIRAF spectra from representative necrotic core, calcified and fatty streak plaques through a double clad fiber ball lens probe according to the exemplary embodiment of the present disclosure. The exemplary raw spectra are shown in FIG. 19(a). The extracted tissue NIRAF spectra are shown in FIG. 19(b), within exemplary emission window of about 680-750 nm. Necrotic core plaques can have a much stronger signal than fiber background.

Figure 20:
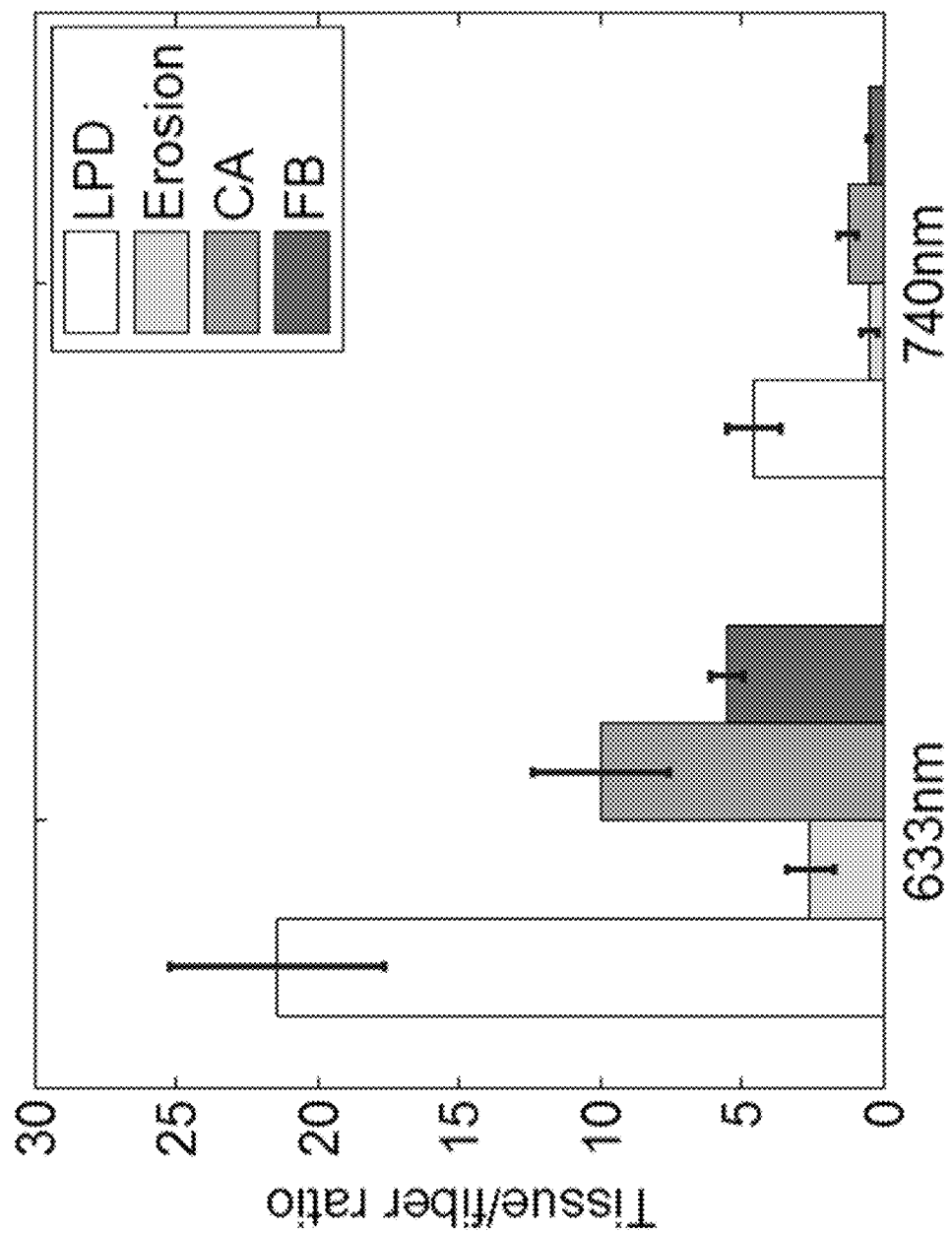
FIG. 20 is a graph of an the exemplary result ratio of integrated autofluorescence and fiber background signals generated by two exemplary NIRAF excitation wavelengths according to the exemplary embodiment of the present disclosure.

FIG. 20 shows a graph of the exemplary ratio of integrated autofluorescence intensities from representative lipid-containing (LPD), erosive (Erosive), calcified (CA) and fibrous (FB) atherosclerotic plaques generated by two exemplary wavelengths at 633 nm and 740 nm. The tissue autofluorescence signal is integrated over the 680-750 nm spectral window to, e.g., exclude the strong silica Raman scattering generated in the double clad fiber. The integration window was selected to maximize the tissue autofluorescence to fiber background ratio.

Figure 21:
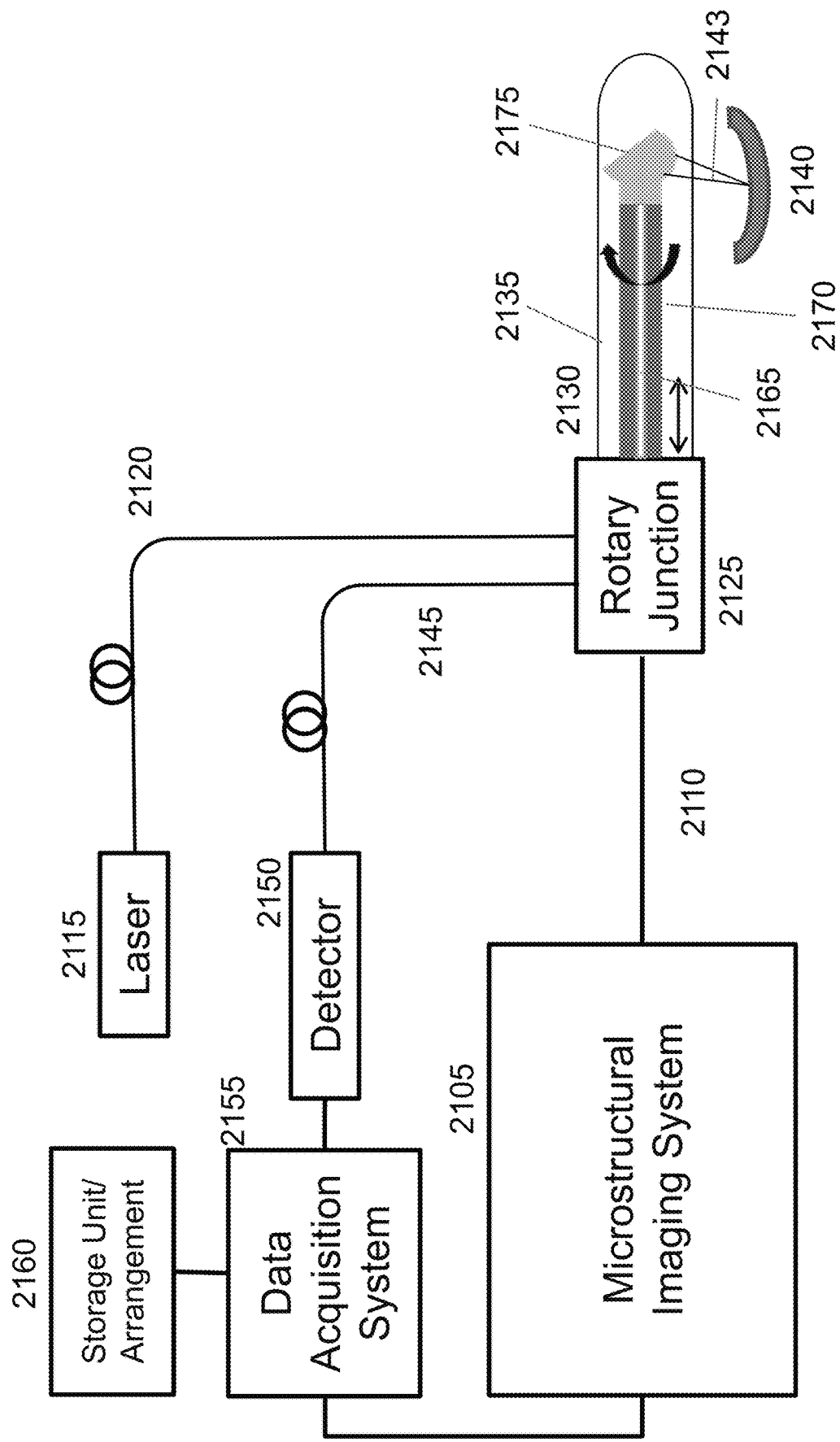
FIG. 21 shows a schematic block diagram of a multimodality OCT-NIRAF catheter imaging system according to an exemplary embodiment of the present disclosure.

NIRAF molecular imaging catheter system can be coupled with other microstructural imaging modalities that can provide a more comprehensive view of the pathological state of the biological tissue. A schematic block diagram of an exemplary embodiment of multimodality NIRAF imaging catheter system according to the present disclosure is shown in FIG. 21. This exemplary apparatus of FIG. 21 can include, e.g., a microstructural imaging system 2105 (which can generate images using one or more processors, as described herein), a single mode optical fiber 2110, an energy source, e.g., a near-infrared laser 2115, an optical fiber 2120, a dual-modality rotary junction 2125, a transparent imaging sheath 2130, a dual-modality optical imaging catheter 2135, a multimode fiber 2145, an optical detector 2150, data acquisition system 2155 and a data processing and storage unit/arrangement 2160. It should be understood that a plurality of each of these described systems, arrangements and elements, or similar devices can be included and/or implemented in or together with the exemplary apparatus of FIG. 21.

The microstructural imaging system 2105 (e.g., one or more systems implementing one or more of optical frequency domain imaging, optical coherence tomography, spectrally encoded confocal microscopy, etc. modalities)

can detect a back-reflected light from a tissue 2140 to acquire information and signals regarding tissue microstructures. The NIRAF molecular imaging system can detect specific molecular information from the tissue 2140. The microstructural imaging system 2105 can be connected to the dual-modality rotary junction 2125 by the single mode fiber 2110. A single mode or multimode fiber 2120 can be used to connect the NIRAF laser 2115 to the dual-modality rotary junction 2125. A multimode fiber 2145 can be a preferred optical fiber for connecting the dual-modality rotary junction 2125 to the optical detector 2150 for, e.g., the NIRAF molecular imaging modality to achieve a high light throughput.

The dual modality rotary junction 2125 can combine two different optical beams, and serve as the interface between the stationary imaging systems to the rotating and translating imaging catheter 2135. The multimodality catheter can include a dual clad fiber 2165, driveshaft 2170, and distal focusing optics 2175 enclosed in a transparent imaging sheath 2130. The imaging sheath 2130 can be used to protect the imaging catheter 2135 and the tissue 2140, while the imaging catheter 2135 rotates and translates and performs a helical scanning of the tissue 2140. The optical imaging beam 2143 can be focused by the dual-modality optical imaging catheter 2135 onto the tissue 2140. Returning light signals from the tissue 2140 are detected by the microstructural imaging system 2105 and the optical detector 2150 of the NIRAF molecular imaging system. Both NIRAF and microstructural 2105 systems can be synchronized, and the signals can be acquired simultaneously by the data acquisition system 2155. The data processing and storage unit/arrangement/apparatus 2160 can record and/or process the data in a real-time for the proper operation, and for subsequent visualization and analysis.

The NIRAF molecular imaging system has flexibility in the choice of components. The source 2115 (e.g., NIR laser source) can be operated in either continuous wave or pulsed mode and can be coupled into either an optical fiber 2120 that is either single or multimode. Fibers 2120, 2145 should be selected to have low background emission, for e.g., to improve the tissue signal to background signal ratio. The optical detector 2150 can include an optical filter, an optical assembly, and either a single channel or multichannel detection. Single channel detection can include use of either a photodiode, avalanche photodiode or photomultiplier tube, which can be a preferred embodiment. In the case of single channel detection, the optical assembly can include a first lens to collimate, an intervening optical filter and a second lens to focus the light to the detector. A second embodiment of the optical assembly can consist of a first lens to collimate the light, a dispersing element, for e.g., a prism, or grating, etc., a second lens to focus the dispersed light and a slit to select the spectral bandwidth before optical detection. Multichannel detection schemes and/or configuration can include the use of a spectral dispersing element, for e.g., grating, prism, spectrometer or series of filters, etc, and optical detector. An embodiment of a multichannel detection scheme can include a spectrometer, grating or prism to disperse the NIRAF emission and a charge coupled detector (CCD), electron multiplying charge coupled devices (EMCCD), CMOS camera or multichannel photomultipliers to detect it. A second embodiment is to use a series of dichroic filters arranged such that shortest wavelength band is reflected first, followed by the next shortest band. These spectral bands are then detected by multiple single channel detectors.

It should be understood to one having ordinary skill in the art that, according to the exemplary embodiment of the present disclosure, the exemplary molecular imaging system 2105 can be coupled to and/or integrated with other systems which can utilize non-optical imaging modalities, including but not limited to ultrasound, ultrasound, photoacoustic imaging, etc. so as to improve the imaging and comparison thereof.

Figure 22:
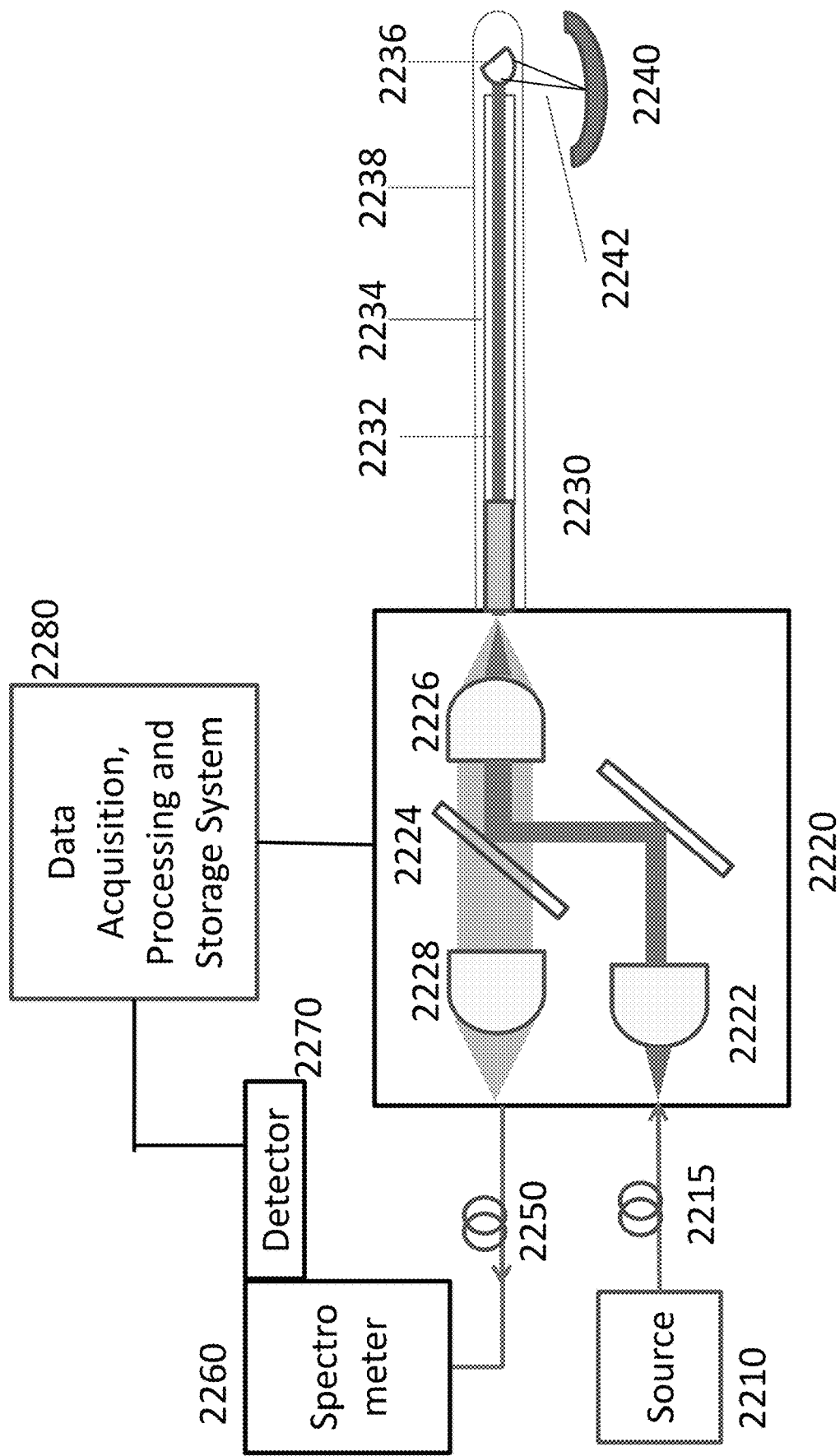
FIG. 22 shows a schematic block diagram of a NIRAF catheter imaging system with multichannel detection according to an exemplary embodiment of the present disclosure.

A schematic diagram of an exemplary embodiment of NIRAF catheter system according to another exemplary embodiment of the present disclosure is shown in FIG. 22. This exemplary apparatus can include a laser or another source of electro-magnetic radiation 2210, optical rotary junction 2220, NIRAF catheter 2230, spectrometer 2260, multichannel detector 2270 and data acquisition and storage system 2280. It should be understood that a plurality of each of these described systems, arrangements and elements, or those similar therto can be included and/or implemented in or together with the exemplary apparatus shown in FIG. 22.

For example, the source (e.g., a NIRAF laser (2210 laser can be connected to the optical rotary junction 2220 by an optical fiber 2215, which can be single-mode or multimode. The optical rotary junction 2220 can serve as the interface between the stationary imaging system to the rotating and translating NIRAF catheter 2230. In the rotary junction 2220, the light is collimated by a lens 2222, filtered by a dichroic mirror 2224 to remove spurious emission from the laser, focused by a second lens 2226 into the NIRAF imaging catheter 2230. The NIRAF catheter 2230 can include an optical fiber 2232, driveshaft 2234, and distal focusing optics 2236 enclosed in a transparent imaging sheath 2238. The optical fiber 2232 can be either a dual clad fiber or a multimode fiber. The imaging sheath 2238 can be used to protect the imaging catheter 2230 and the tissue 2240, while the NIRAF catheter 2230 rotates and translates and performs a helical scanning of the tissue 2240. The optical imaging beam 2242 can be focused by the NIRAF catheter 2230 onto the tissue 2240. Returning light signals from the tissue 2240 are returned through the optical rotary junction 2230, filtered by the dichroic mirror 2224, coupled by a third lens 2228 into a multimode fiber 2250, delivered to the spectrometer 2260 and detected a multichannel detector 2270. The multichannel detector 2270 can be or include a multichannel photomultiplier tube, a charge coupled device (CCD), an electron multiplying charge coupled device (EMCCD), and/or CMOS camera. The data processing and storage apparatus/system 2280 can be connected to the multichannel detector 2270 and the optical rotary junction 2220. The data processing and storage apparatus/system 2280 can record and/or process the data in a real-time for the proper operation, and for subsequent visualization and analysis.

Figure 23:
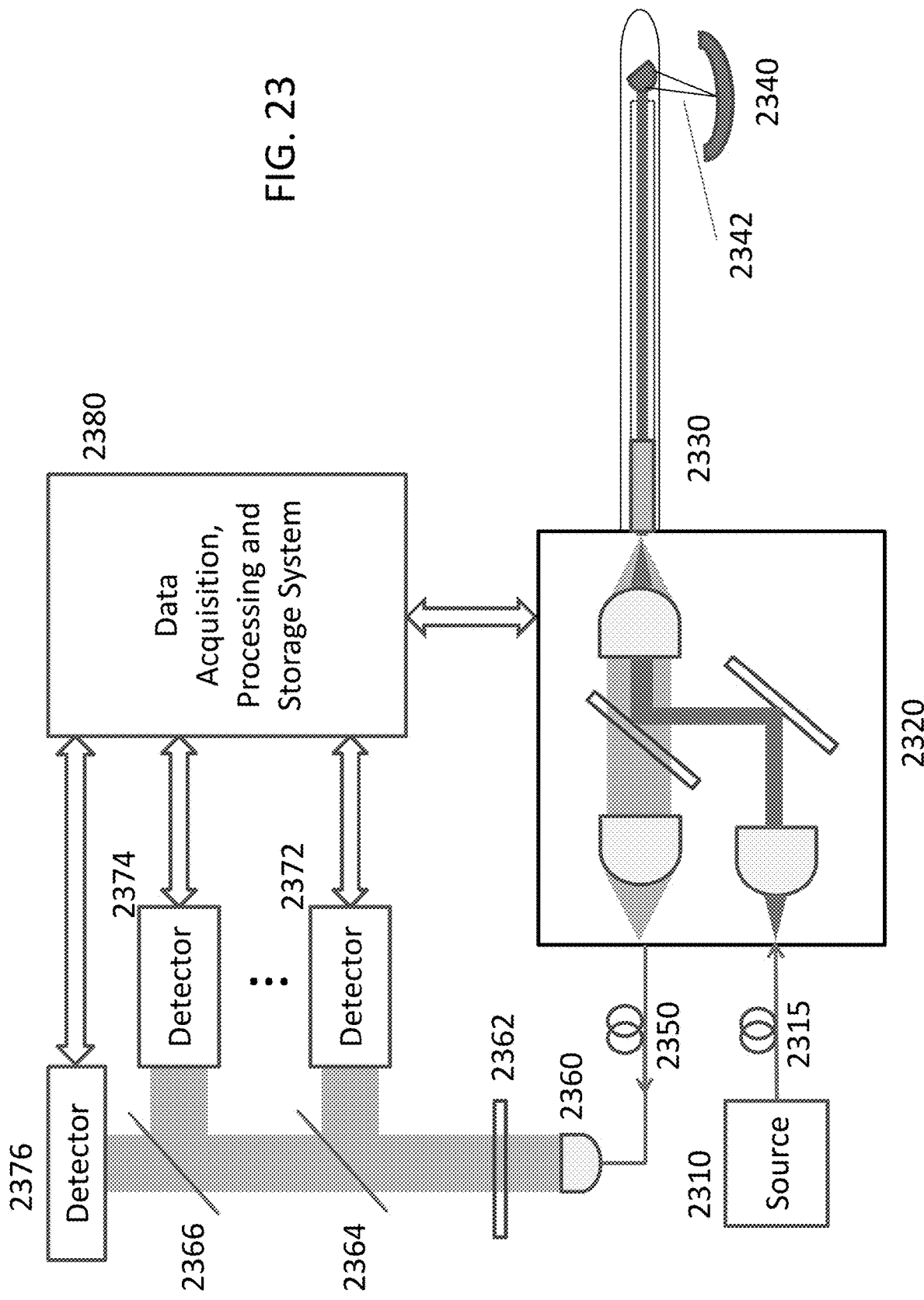
FIG. 23 shows a schematic block diagram of a NIRAF catheter imaging system with multiple dichroic mirrors for spectral ratio acquisition.

Exemplary calculations/determinations of the spectral ratio can be achieved using a multiple dichroic mirror and single channel detector scheme where the position and width of the spectral band detected is controlled by the selection of the wavelength-dependent transmission and reflection properties of the dichroic mirror arranged in series. A schematic diagram of another exemplary embodiment of NIRAF catheter system according to the present disclosure is shown in FIG. 23. This exemplary apparatus can include a laser or a source of electro-magnetic radiation 2310, optical rotary junction 2320, NIRAF catheter 2330, multiple filter assembly, multiple single channel detectors 2370, 2372, 2374 and data acquisition and storage system 2380. It should be understood that a plurality of each of these described systems, arrangements and elements, or those similar thereto, can be included and/or implemented in and/or together with the exemplary apparatus shown in FIG. 23.

Similar to the exemplary embodiment shown in FIG. 22, the source (e.g., a NIRAF laser) 2310 laser is connected to the optical rotary junction 2320 by an optical fiber 2315, which can be either single-mode or multimode. The optical rotary junction 2320 can serve as the interface between the stationary imaging system to the rotating and translating NIRAF catheter 2330. The optical imaging beam 2342 can be focused by the NIRAF catheter 2330 onto the tissue 2340. Returning light signals from the tissue 2340 are returned through the optical rotary junction 2330, coupled into a multimode fiber 2350, and delivered to multiple filter assembly. The multiple filter assembly can include a collimating lens 2360, a long-pass filter 2362, a dichroic mirror at a shortest wavelength cutoff 2364, and a dichroic mirror at a longer wavelength cutoff 2366. Each dichroic mirror 2364, 2366 can be paired with a single channel detector 2372, 2374 and an additional detector 2376, which receives the longest wavelengths. FIG. 23 illustrates an exemplary three channel detection system. Nonetheless, it should be understood that it is possible to increase the number of channels by increasing the number of filtering stages and detectors. The data processing and storage apparatus/system 2380 can be connected to the multiple detectors and the optical rotary junction 2320. The data processing and storage apparatus/system 2280 can record and/or process the data in a real-time for the proper operation, and for subsequent visualization and analysis.

Figure 24:
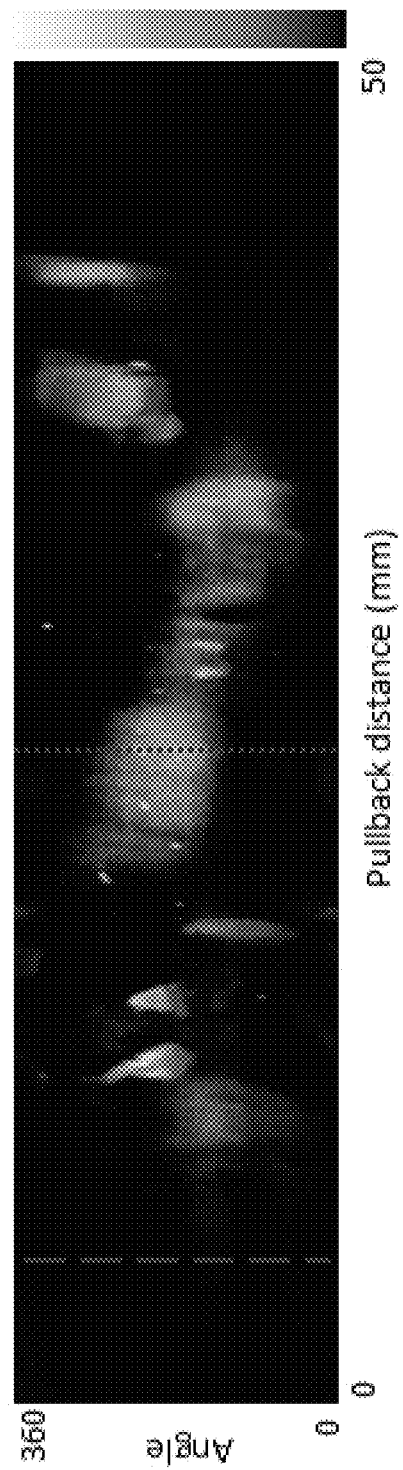
FIG. 24 shows a representative image of a 2D-NIRAF en face intensity map according to an exemplary embodiment of the present disclosure.

FIG. 24 shows a representative imaging of a 2-D NIRAF en face intensity map obtained from an exemplary human coronary artery using a multimodality OCT-NIRAF system and catheter as described herein with reference to the diagram of FIG. 21. In this example, a fresh explant human heart imaged within 24 hours after the harvest procedure was used in the ex vivo imaging study. Before OCT-NIRAF imaging, the lumen was flushed with 10% phosphate buffered saline solution to facilitate catheter access and to maintain the natural diameter of the coronary lumen. The x-axis of the 2D NIRAF intensity map corresponds to the longitudinal pullback position, and the y-axis, the scanning angle (i.e., 0 to 360 degrees). In the image, the dashed line corresponds to intimal hyperplasia while the dotted line is a calcified plaque. The vertical axis is the imaging angle (0 to 360 degrees) and the horizontal axis is the pullback direction (0 to 50 mm). Image orientation is distal (left side) to proximal (right side) portion of the vessel. The color map ranges from blue (low NIRAF intensity) to green, yellow and white (highest NIRAF intensity).

Figure 25B:
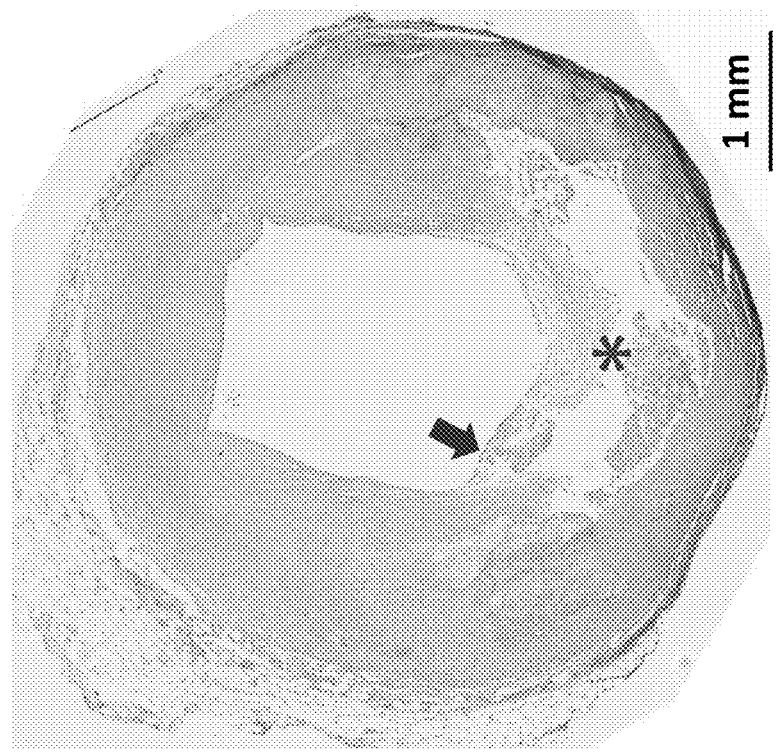
FIG. 25(a)-25(b) is an exemplary composite OCT-NIRAF image and the corresponding histology from obtained from a ruptured necrotic core plaque according to an exemplary embodiment of the present disclosure.
Figure 25A:
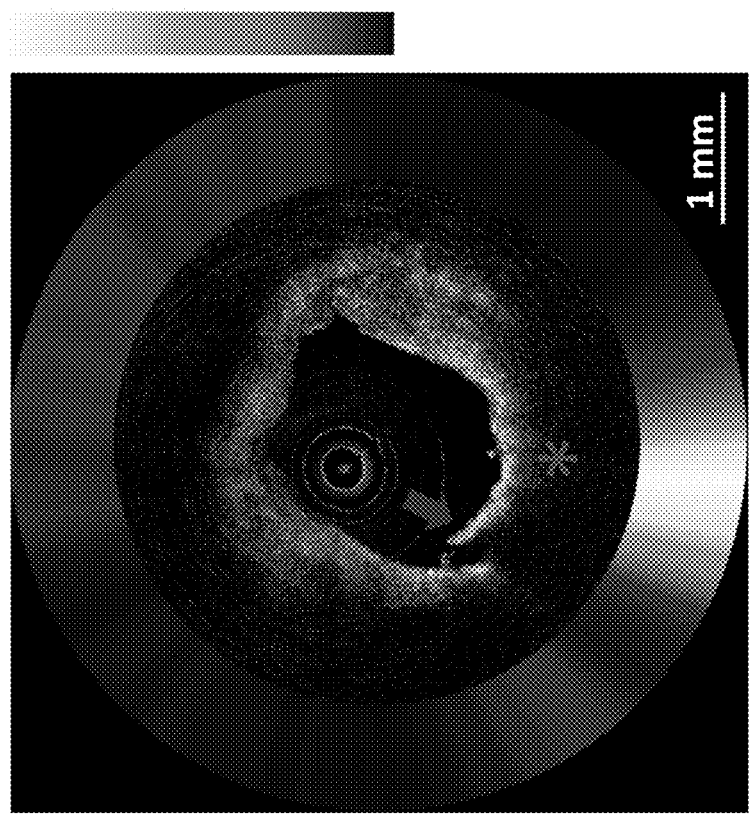

FIGS. 25(a) and 25(b) illustrate a set of exemplary images of a composite OCT-NIRAF image extracted from a comprehensively scanned coronary artery and the corresponding histology section for a ruptured necrotic core plaque. The OCT-NIRAF image was generated using a multimodality OCT-NIRAF system and catheter as described herein and shown in FIG. 21. In the exemplary OCT-NIRAF image (see FIG. 25(a)), the OCT image indicates the presence of a plaque rupture (arrow) and area of high attenuation suggestive of a lipid pool or necrotic core (star). The NIRAF signal is high at over the necrotic core location with good contrast. In the corresponding histology image (see FIG. 25(b)), the H&E stained section confirms that the plaque is a ruptured thin-capped fiberatheroma. The scale bars for both images are 1 mm. This exemplary result can demonstrate co-registered intracoronary OCT and NIRAF imaging in living human patients undergoing percutaneous catheterization as a standard of care and provides microstructural and fluorescence imaging of biomarkers related to inflammatory responses and oxidative stress.

Figure 26:
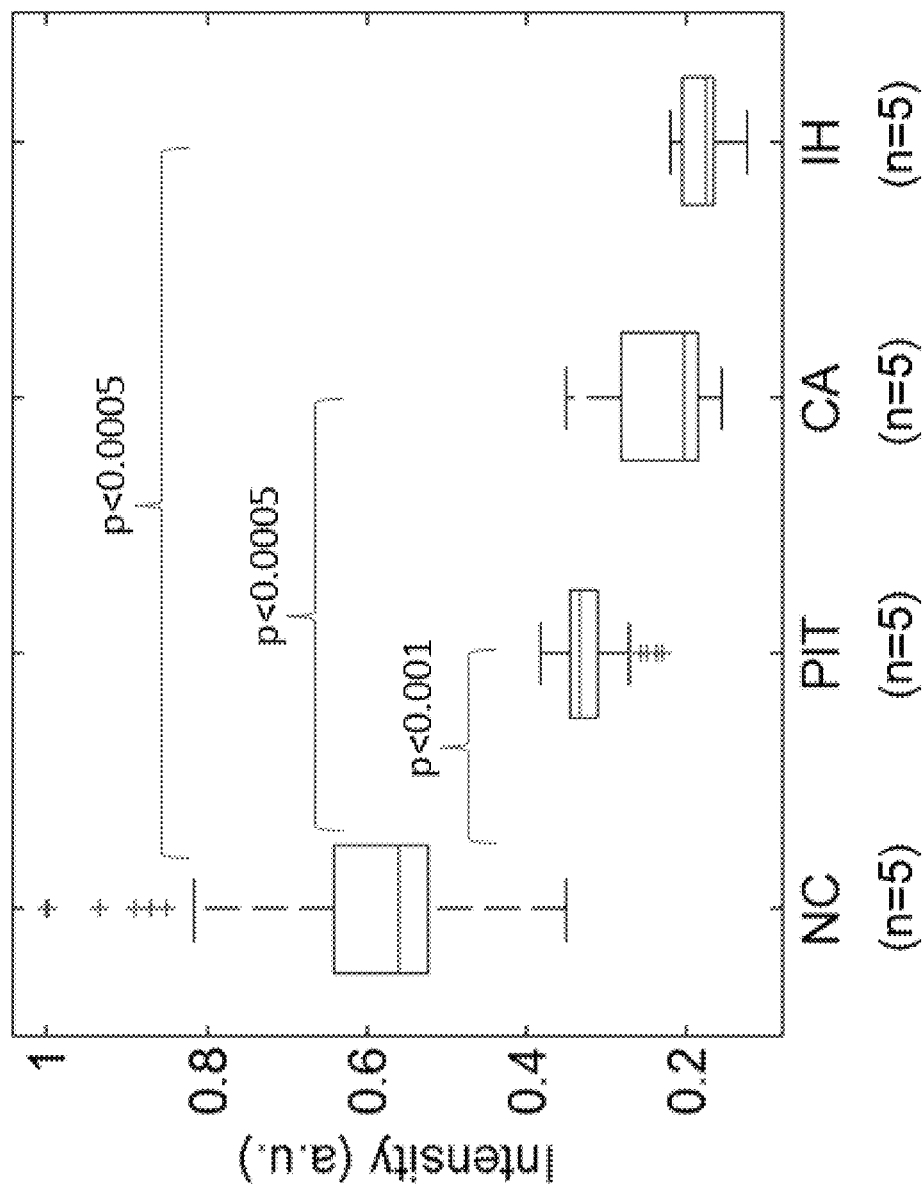
FIG. 26 is a whisker box plot illustrating the NIRAF intensity obtained through an intracoronary catheter for different pathological classification.

FIG. 26 shows a whisker box plot of the exemplary representation of the catheter-based NIRAF signal intensities for different coronary lesion types including necrotic core (NC), pathological intimal thickening (PIT), calcification (CA) and intimal hyperplasia (IH). NIRAF intensities were acquired from diseased human coronary arteries ex vivo using as described using a multimodality OCT-NIRAF system and catheter as described herein and shown in FIG. 21. NIRAF intensities from NC, PIT, CA and IH, were statistically significantly different according to one-way ANOVA ($p<0.0005$). Using a Student's t-test, the NIRAF intensity of NC plaques was significantly higher than those from non-necrotic lesions ($p<0.0005$). Calcified plaques in the coronary arteries showed slightly higher NIRAF than PIT. One possible reason for this finding is that the calcified coronary plaques in this study were advanced and coexisted with significant extracellular lipid. These results indicate that NIRAF can differentiate NC and non-NC plaques (CA and PIT) in coronary arteries In addition, the exemplary embodiments of the present disclosure can be used for analysis and/or treatment of other disease, including, e.g., cancer and neurodenerative diseases.

Figure 27:
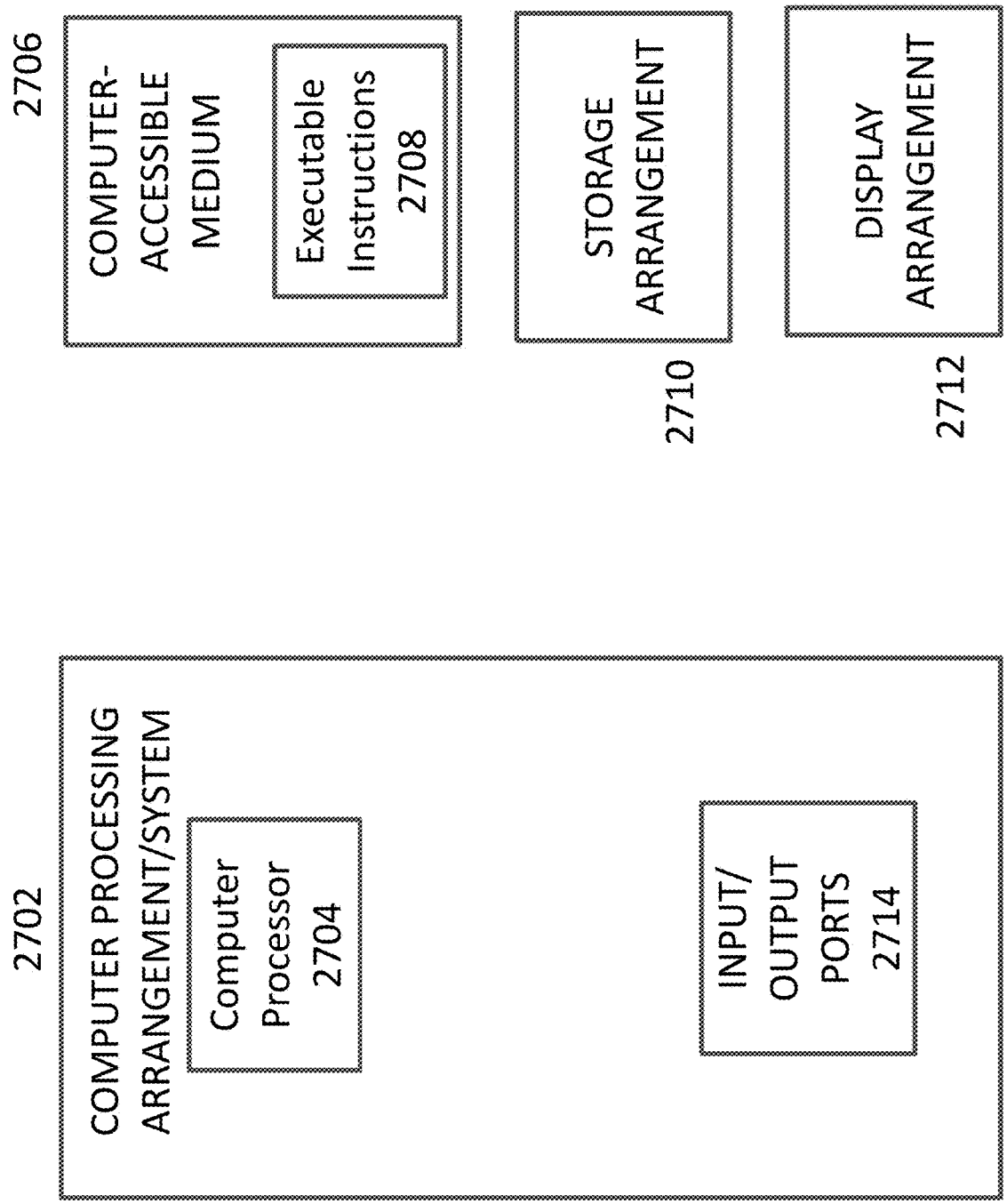
FIG. 27 is an exemplary block diagram of an exemplary system in accordance with certain exemplary embodiments of the present disclosure.

FIG. 27 shows a block diagram of an exemplary embodiment of a system according to the present disclosure. For example, exemplary procedures in accordance with the present disclosure described herein can be performed by a processing arrangement and/or a computing arrangement 2702. Such processing/computing arrangement/system 2702 can be, for example, entirely or a part of, or include, but not limited to, a computer/processor 2704 that can include, for example, one or more microprocessors, and use instructions stored on a computer-accessible medium (e.g., RAM, ROM, hard drive, or other storage device).

As shown in FIG. 27, for example, a computer-accessible medium 2706 (e.g., as described herein above, a storage device such as a hard disk, floppy disk, memory stick, CD-ROM, RAM, ROM, an optical disk (such as a compact disc (CD), digital versatile disc (DVD), or Blu-ray Disc (BD)™), a flash memory device, a memory card, and the like, etc., or a collection thereof) can be provided (e.g., in communication with the processing arrangement 2702). The computer-accessible medium 2706 can contain executable instructions 2708 thereon. In addition or alternatively, a storage arrangement 2710 can be provided separately from the computer-accessible medium 2706, which can provide the instructions to the processing arrangement 2702 so as to configure the processing arrangement to execute certain exemplary procedures, processes and methods, as described herein above, for example.

Further, the exemplary processing arrangement 2702 can be provided with or include an input/output interface/arrangement 2714, which can include, for example, a wired network, a wireless network, the internet, an intranet, a data collection probe, a sensor, etc. An I/O interface/arrangement 2714 can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless). As shown in FIG. 27, the exemplary processing arrangement 2702 can be in communication with an exemplary display arrangement 2712, which, according to certain exemplary embodiments of the present disclosure, can be a touch-screen configured for inputting information to the processing arrangement in addition to outputting information from the processing arrangement, for example. Further, the exemplary display 2712 and/or a storage arrangement 2710 can be used to display and/or store data in a user-accessible format and/or user-readable format.

A detector interface can also be provided to work with the I/O interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on the computer-accessible medium 2706.

Figure 28:
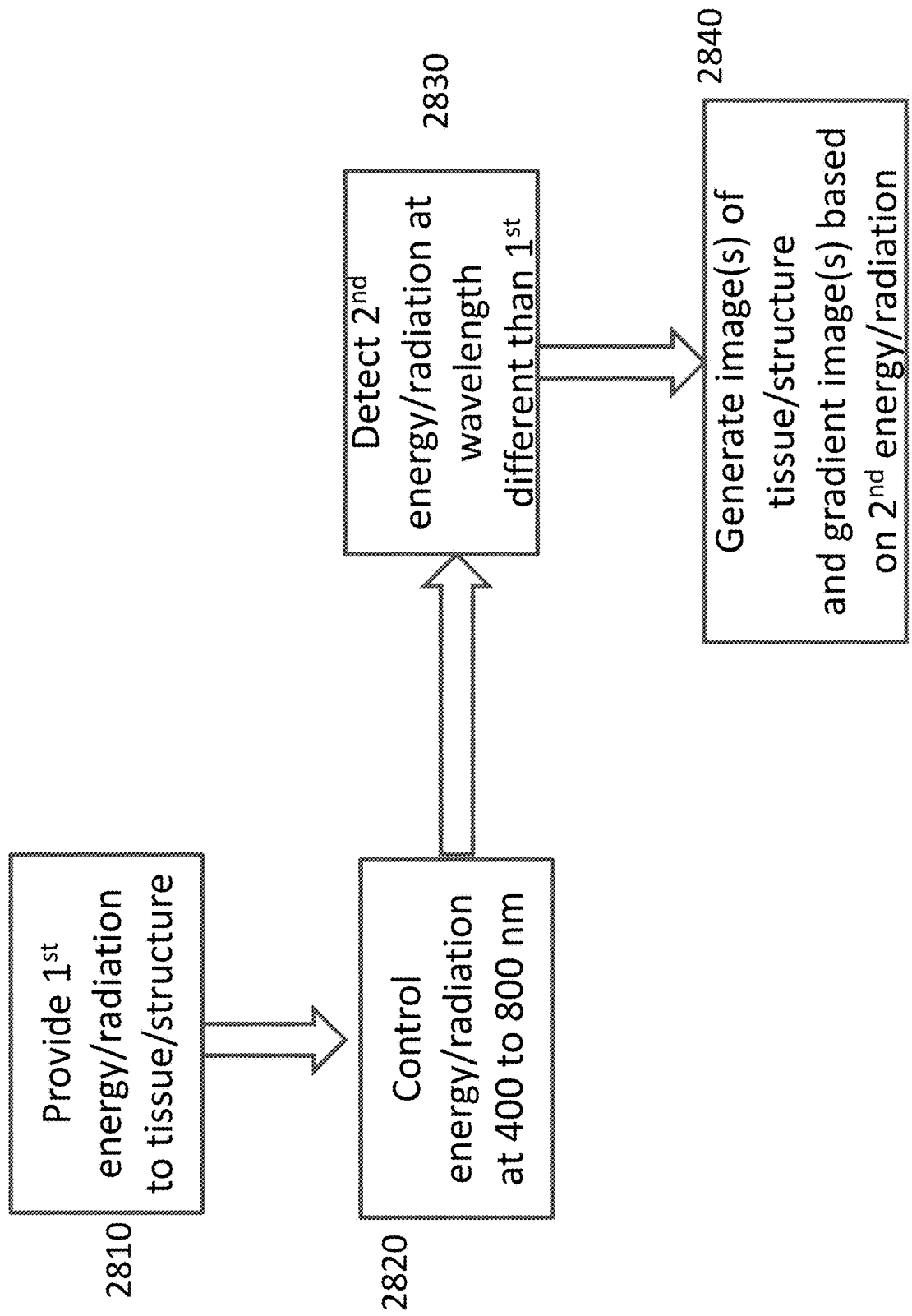
FIG. 28 is an exemplary flow diagram of another method according to a further exemplary embodiment of the present disclosure.

According to yet another exemplary embodiment of the present disclosure, an apparatus and method can be provided, as shown in a flow diagram of FIG. 28. For example, with an energy source, it is possible to provide at least one first light radiation to a structure at at least one first wavelength (procedure 2810). The wavelength can be controlled to be between 400 nm and 800 nm (procedure 2820). With a detector arrangement, it is possible to detect at least one second light radiation at at least one second wavelength which is different from the first wavelength (procedure 2830). The second light radiation can be based on an autofluorescence of at least one portion of the structure being impacted by the first light radiation. Further, with a computer arrangement, it is possible to generate at least one first image of the portion(s) of the structure and at least one gradient second image based on the second light radiation (procedure 2840).

For example, the first or second images can be co-registered. The generation procedure can comprises obtaining an OCT image, an IVIS image, an angiographic image, a CT image, or an MRI image. The second image can include a display of a ratio of at least two wavelength ranges of the second light radiation.

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements and methods which, although not explicitly shown or described herein, embody the principles of the disclosure and are thus within the spirit and scope of the present disclosure. In addition, to the extent that the prior art knowledge has not been explicitly incorporated by reference herein above, it is explicitly being incorporated herein in its entirety. Further, the exemplary embodiments described herein can operate together with one another and interchangeably therewith. All publications referenced herein above are incorporated herein by reference in their entireties.

EXEMPLARY REFERENCES

The following references are hereby incorporated by reference in their entireties:
1. Signore A, Mather S J, Piaggio G, Malviya G and Dierckx R A. Molecular Imaging of Inflammation/Infection: Nuclear Medicine and Optical Imaging Agents and Methods. *Chemical Reviews*. 2010; 110:3112-3145.
2. Su H S, Nahrendorf M, Panizzi P, Breckwoldt M O, Rodriguez E, Iwamoto Y, Aikawa E, Weissleder R and Chen J W. Vasculitis: Molecular Imaging by Targeting the Inflammatory Enzyme Myeloperoxidase. *Radiology*. 2012; 262:181-190.

What is claimed is:

1. An apparatus, comprising:
a catheter configured and structured to be inserted into a blood vessel;
an energy source arrangement configured to provide at least one first light radiation through the catheter to the blood vessel at at least one first visible wavelength;
a detector arrangement configured to detect at least one second light radiation through the catheter at at least one second near-infrared wavelength that is different from the at least one first wavelength, wherein the at least one second light radiation is based on an autofluorescence of at least one portion of the blood vessel being impacted by the at least one first light radiation; and
a computer arrangement configured to determine at least one characteristic of the blood vessel indicative of inflammation based on the autofluorescence,
the determining procedure including processing the detector signal based on the at least one second light radiation to further determine the at least one characteristic.

2. The apparatus of claim 1, wherein the at least one visible wavelength comprises a visible red wavelength.

3. The apparatus of claim 2, wherein the at least one visible red wavelength comprises 633 nm.

4. A method comprising:
inserting a catheter into a blood vessel;
providing, through the catheter, at least one first light radiation to the blood vessel at at least one first wavelength that is between 550 nm and 900 nm;
detecting, through the catheter, at least one second light radiation at at least one second wavelength that is between 640 nm and 900 nm, wherein the at least one second light radiation is based on an autofluorescence of at least one portion of the blood vessel being impacted by the at least one first light radiation; and
determining, based on the autofluorescence, at least one characteristic of the blood vessel indicative of inflammation,
the determining procedure including processing the detected signal based on the at least one second light radiation to further determine the at least one characteristic.

5. The method of claim 4, wherein the at least one characteristic comprises at least one of oxidative stress, calcium, intraplaque hemorrhage, protein modification, lipoprotein modification, lipid modification, or enzymatic activity.

6. The method of claim 4, wherein the first wavelength is between 600 nm and 700 nm.

7. The method of claim 4, wherein the determining procedure includes a mathematical manipulation of an emission spectrum of the second radiation to further determine the at least one characteristic.

8. The method of claim 4, wherein the protein modification is dityrosine or nitrotyrosine.

9. The method of claim 4, wherein the lipo-protein modification is oxidized LDL.

10. The method of claim 4, wherein the intraplaque hemorrhage contains endogenous porphyrins.

11. The method of claim 4, further comprising providing at least one third radiation to the sample and at least one fourth radiation to a reference, and receiving at least one fifth radiation that is an interference between the third and fourth radiations, wherein the determination is performed as a further function of the fifth radiation.

12. The method of claim 11, wherein the fifth radiation is at least partially co-localized with the first radiation.

13. The method of claim 4, wherein the blood vessel is in a patient suspected of having necrotic plaque.

14. The method of claim 4, wherein determining procedure comprises:
    detecting at least two second wavelength ranges,
    characterizing a spectral shape data or a relative intensity data with the at least two second wavelength ranges, and
    comparing the spectral shape or relative intensity data to a training data set.

15. The method of claim 14, wherein the spectral shape data is compared as a ratio of the at least two second wavelength ranges.

16. The method of claim 14, wherein the spectral shape data or the relative intensity data are calibrated with noise or sensor parameters.

17. The method of claim 14, wherein the characterizing process comprises analyzing with a principal component analysis method.

18. The method of claim 4, wherein the determining procedure comprises:
    detecting the plurality of second wavelengths;
    scoring a spectral shape and relative intensity with the second wavelengths, and
    comparing a third score to a training data set.

19. An apparatus, comprising:
    a catheter configured and structured to be inserted into a blood vessel;
    an energy source arrangement configured to provide, through the catheter, at least one first light radiation to the blood vessel at at least one first wavelength that is between 550 nm and 800 nm;
    a detector arrangement configured to detect, through the catheter, at least one second light radiation at at least one second wavelength that is between 640 nm and 900 nm, wherein the at least one second light radiation is based on an autofluorescence of at least one portion of the blood vessel being impacted by the at least one first light radiation; and
    a computer arrangement configured to determine at least one characteristic of the blood vessel indicative of inflammation based on the autofluorescence,
        the determining procedure including processing the detected signal based on the at least one second light radiation to further determine the at least one characteristic.

20. The apparatus of claim 19, wherein the at least one characteristic comprises at least one of oxidative stress, calcium, intraplaque hemorrhage, protein modification, lipo-protein modification, lipid modification, or enzymatic activity.

21. An imaging method, comprising:
    providing at least one first light radiation to a structure at at least one first wavelength that is between 600 and 900 nm;
    detecting at least one second light radiation at at least one second wavelength which is different from the first wavelength, wherein the second light radiation is based on an auto fluorescence of at least one portion of the structure being impacted by the first light radiation; and
    generating at least one first image of the at least one portion of the structure and at least one gradient second image based on the autofluorescence,
        wherein the at least one first image or the at least one gradient second image includes information identifying at least one characteristic indicative of inflammation in the at least one portion of the structure,
        wherein the at least one characteristic indicative of inflammation is determined by processing the detected signal based on the at least one second light radiation to further determine the at least one characteristic.

22. The imaging method of claim 21, wherein at least one of the first image or the at least one gradient second image is co-registered.

23. The imaging method of claim 21, wherein the generation procedure comprises obtaining an OCT image, an IVIS image, an angiographic image, a CT image, or an MM image.

24. The imaging method of claim 21, wherein the at least one gradient second image includes a display of a ratio of at least two wavelength ranges of the second light radiation.

* * * * *

UNITED STATES PATENT AND TRADEMARK OFFICE
CERTIFICATE OF CORRECTION

| | |
|---|---|
| PATENT NO. | : 11,890,077 B2 |
| APPLICATION NO. | : 17/161366 |
| DATED | : February 6, 2024 |
| INVENTOR(S) | : Hao Wang et al. |

It is certified that error appears in the above-identified patent and that said Letters Patent is hereby corrected as shown below:

In the Specification

Column 12, Line 40, ">1H" should be -->IH--.

In the Claims

Column 22, Claim 23, Line 45, "MM" should be --MRI--.

Signed and Sealed this
Eleventh Day of June, 2024

Katherine Kelly Vidal
*Director of the United States Patent and Trademark Office*